United States Patent [19]
Haugland et al.

[11] Patent Number: 5,616,502
[45] Date of Patent: Apr. 1, 1997

[54] NON-SPECIFIC PROTEIN STAINING USING MEROCYANINE DYES

[75] Inventors: Richard P. Haugland; Victoria L. Singer, both of Eugene; Laurie J. Jones, Monroe; Thomas H. Steinberg, Eugene, all of Oreg.

[73] Assignee: Molecular Probes, Inc., Eugene, Oreg.

[21] Appl. No.: 444,895

[22] Filed: May 19, 1995

[51] Int. Cl.$^6$ ............................ G01N 33/48; G01N 33/52; G01N 33/68
[52] U.S. Cl. ...................... 436/86; 436/87; 436/88; 436/164; 436/166; 436/172; 436/175; 436/177; 422/61
[58] Field of Search .................... 436/86–88, 164, 436/166, 172, 175, 177; 422/61

[56] References Cited

U.S. PATENT DOCUMENTS

| | | | |
|---|---|---|---|
| 4,337,063 | 6/1982 | Mihara et al. | 23/320 B |
| 4,424,201 | 1/1984 | Valinsky et al. | 424/3 |
| 4,886,744 | 12/1989 | Arnost et al. | 435/6 |
| 5,122,602 | 6/1992 | Corey et al. | 536/17.2 |
| 5,182,214 | 1/1993 | Kessler et al. | 436/88 |
| 5,264,589 | 11/1993 | Corey et al. | 548/51 |
| 5,268,486 | 12/1993 | Waggoner et al. | |
| 5,279,790 | 1/1994 | Corey et al. | 422/56 |
| 5,321,130 | 6/1994 | Yue et al. | |
| 5,410,030 | 4/1995 | Yue et al. | |

FOREIGN PATENT DOCUMENTS

| | | |
|---|---|---|
| 517055 | 12/1992 | European Pat. Off. |
| 517050 | 12/1992 | European Pat. Off. |
| 6-123740 | 5/1994 | Japan |
| WO93/06482 | 4/1993 | WIPO |

OTHER PUBLICATIONS

A. Hassner et al. *J. Org. Chem* 1984, 49, 2546–2551.
L. G. S. Brooker et al. *J. Am. Chem. Soc.* 1951, 73, 5350–5356.
M. Gemählich et al. *Z. Ges. Exptl. Med.* 1958, 130, 312–318.
J. C. Smith *Biochim. Biophys, Acta* 1990, 1016, 1–28.
R. Buehler et al. *J. Membr. Biol.* 1991, 121, 141–161.
D. K. Gaffney et al. *Biochim. Biophys. Acta* 1992, 1117, 321–325.
V.A. Izmail'skii et al. *J. Gen. Chem. USSR* 1959, 29, 1813–1819.
R.D. Strickland et al. *Anal. Chem.* 1959, 31, 1408–1410.
M. Gemählich et al, *Chem. Abstr.* 1960, 54, 21215d.
E.G. McRae et al. Chem. Abstr. 1965 63, 2525g.
Y.X. Ci et al. *Analyst,* 1988, 113, 679–681.
K.M. Hahn et al. *J. Biol. Chem.* 1990, 265, 20335–20345.
J.C. Smith *Chem. Abstr.* 1990, 112, 174955m.
R. Buehler et al. *Chem. Abstr.* 1991, 115, 87596p.
D.K. Gaffney et al. *Chem. Abstr.* 1992, 117, 247851q.
A.C. Stevens et al. *Bioconjugate Chem.* 1993, 4, 19–24.
R.J. Williams et al. *Anal. Chem.* 1993, 65, 601–605.
T.A. Vida et al, *J. Cell. Biol.* 1995, 128, 779–792.
N.V. Visser et al. *Biochemistry* 1995, 34, 11777–11784.
Daban, et al., Anal. Biochem. 199, 169 (1991).
Lowry, et al., J. Biol. Chem., 193, 265 (1951).
Smith, et al., Anal. Biochem., 150, 76 (1985).
Bradford, Anal. Biochem., 72, 248 (1976).
Daban, et al., Anal. Biochem., 199, 162 (1991).
Grinvald, et al., Biophys. J. 39, 301 (1982).
Loew, et al., J. Org. Chem. 49, 2546 (1984).
Brooker, et al., J. Am. Chem. Soc. 73, 5326 (1951).

*Primary Examiner*—Arlen Soderquist
*Attorney, Agent, or Firm*—Allegra J. Helfenstein; Anton E. Skaugset

[57] ABSTRACT

The present invention describes the use of a variety of merocyanine dyes and substituted merocyanine dyes for detecting and quantifying poly(amino acids), including peptides, polypeptides and proteins. The labeled proteins or peptides are highly colored, but are also detected by their strong fluorescence enhancement. Poly(amino acids) are detected in solution, in electrophoretic gels, and on solid supports, including blots and dipsticks. The present method of staining is highly sensitive, extremely facile, and relatively non-selective.

38 Claims, 6 Drawing Sheets

NON-SPECIFIC PROTEIN STAINING USING MEROCYANINE DYES

FIELD OF THE INVENTION

The invention relates to the staining of poly(amino acids), including peptides, polypeptides and proteins in solution, in gels and on solid supports, using merocyanine dyes.

BACKGROUND

Detection and analysis of poly(amino acids) is of great importance in a multitude of diverse activities, ranging from commercial enzyme production, forensics analysis and diagnostics to basic research in biochemistry, molecular biology, neuroscience, developmental biology or physiology. As used herein, a poly(amino acid) is any homopolymer or heteropolymer of amino acids, including peptides and proteins. Primarily, poly(amino acids) are detected and characterized using gel electrophoresis, by solution quantitation assays or by detection on solid supports, such as filter membranes.

Electrophoresis of poly(amino acids) is most commonly carried out using polyacrylamide gels. Unmodified protein or other poly(amino acid) bands in gels are generally not visible to the naked eye. Thus, for electrophoretic gels to be useful, the bands or spots must be stained, so that they can be localized and identified. Two of the most common methods of staining poly(amino acids) on gels are COOMASSIE Brilliant Blue staining (hereafter referred to as CBB staining) and silver staining.

For CBB staining, the electrophoresis gel is first fixed, stained for several hours with a triphenylmethane-based dye, then destained for several more hours. The resulting stained gel is pale blue with dark blue bands containing the poly(amino acids). The sensitivity of CBB staining is strongly dependent on how thoroughly the gel is destained. A destaining period of 24 hours typically allows as little as 0.03–0.1 µg of poly(amino acid) to be detected in a single band. However, excessive destaining also results in signal loss from the bands. Although CBB staining is inexpensive, easy to use, and the resulting gels are easily preserved, CBB staining gives linear responses within only a narrow dynamic range. Furthermore, once stained using CBB, the poly(amino acids) in the gel cannot be blotted for immunoanalysis, CBB staining is somewhat selective for poly(amino acid) composition and tends to bind small peptides poorly.

Silver staining utilizes the differential reduction of silver ions bound to the side chains of amino acids in poly(amino acids). For particular poly(amino acids), silver staining is approximately 100- to 1000-fold more sensitive than CBB staining and is capable of detecting 0.1–1 ng of poly(amino acid) in a single band. A gel that has been silver stained is clear to yellow-tan, with gray, dark-brown or black poly(amino acid) bands. Silver stained gels can readily preserved, as for CBB stained gels. Like CBB staining, silver staining is time-consuming and yields a narrow linear response for densitometric quantitation. Also, the stained gels cannot be blotted for further analysis. In addition, silver staining requires the handling of several very toxic, unstable and expensive solutions, and the resulting staining is extremely selective for poly(amino acid) composition, both in band color and band intensity. Finally, silver staining requires an exacting methodology that is often difficult to perform reproducibly.

A relatively recent method for staining protein gels uses the dye Nile red (9-diethylamino-5H-benzo(α)phenoxazine-5-one) as a fluorescent stain for the poly(amino acid) bands in SDS-polyacrylamide gels (Daban et al., ANAL. BIOCHEM. 199, 169 (1991)). The use of Nile red as a stain for poly(amino acids) on gels is rapid, does not require that the gel be fixed prior to staining, and the resulting stained gels can be blotted for further analysis. However, Nile red-stained gels photobleach rapidly, requiring gels to be documented immediately with photography. The use of Nile red in combination with black and white POLAROID photography is capable of detecting 30 ng of poly(amino acid) in a single band, putting its sensitivity between that of CBB staining and silver staining. Finally, Nile red itself is very insoluble, resulting in poor penetration of gel bands and making staining solutions difficult to handle, Use of the present invention possesses many advantages over known methods for staining poly(amino acids) on gels: Staining is very rapid, and is relatively insensitive to poly(amino acid) composition. Visualization of stained gels is possible without destaining, and the stained bands remain readily detectable for several days. The dyes used in the current method are readily soluble and stable in aqueous staining solutions. In addition, the dyes exhibit a large Stokes shift between the absorbance and emission maxima. Finally, the staining procedure of the present invention is rapid and simple, requires minimal labor, and allows the detection of as little as 1 ng of poly(amino acid) per band; this sensitivity is in many cases equal to or better than that of silver staining, with far less hazard and expense, and is more than an order of magnitude better than CBB or Nile red staining.

The dyes of the present invention can also be used to detect poly(amino acids) on filter membranes or other solid supports, or in solution. The use of the dyes of the current invention for staining poly(amino acids) in solution can be used to quantitate poly(amino acids) with greater sensitivity than other known methods (Table 3), including absorbance-based methods, such as the Lowry method (J. BIOL. CHEM., 193, 265 (1951)), the bicinchoninic acid (BCA) method (ANAL, BIOCHEM., 150, 76 (1985)), and the Bradford method (ANAL. BIOCHEM., 72, 248 (1976)); and fluorescence-based methods, such as those employing Nile red (ANAL. BIOCHEM, 199, 162 (1991)). Using preferred embodiments of this new solution assay, the linear dynamic range for quantitation extends over almost three orders of magnitude in poly(amino acid) concentration (from about 30 ng/mL to about 10 µg/mL, see Table 2), in contrast to the more limited range of the well-known Lowry (0.1–2 mg/mL), Bradford (0.2–1.4 mg/mL), and BCA (10–2000 µg/mL) methods. The solution assay of the present invention is simple and suitable for use with either standard fluorometers or automated microtiter plate readers, or can be modified for use with electrophoretic capillaries or density gradients.

The preparation and characterization of the merocyanine dyes of the present invention has been well documented. A large number of useful styryl merocyanine dyes (commonly referred to as RH dyes) have been previously prepared by Rina Hildesheim (Grinvald et al., BIOPHYS. J. 39, 301 (1982), incorporated by reference), Leslie Loew (Loew et al., J. ORG. CHEM. 49, 2546 (1984), incorporated by reference) and others, as useful probes for measuring electric potentials in cell membranes. Useful membrane potential measurements only occur in live cells and artificial liposomes, where the fluorescence intensity of a suitable dye as it is associated with the membrane changes as the membrane is subjected to an electrical gradient. In addition to the above membrane potential probes, an extensive variety of other merocyanine dyes have been described by Brooker et al. (J. AM. CHEM. SOC. 73, 5326 (1951), incorporated by reference), primarily for use in the photographic industry, although Brooker et al. do not describe the fluorescence properties of the merocyanines. The present invention describes the use of these and other reagents to label and detect poly(amino acids), including cellular components, outside of the cellular milieu. This novel use of merocyanine dyes, which is faster, easier, less expensive, and less hazardous than other known methods of staining poly(amino acids), is neither anticipated nor obvious from previously described uses.

SUMMARY OF THE INVENTION AND DESCRIPTION OF PREFERRED EMBODIMENTS

Selection of Dyes

Figure 1:
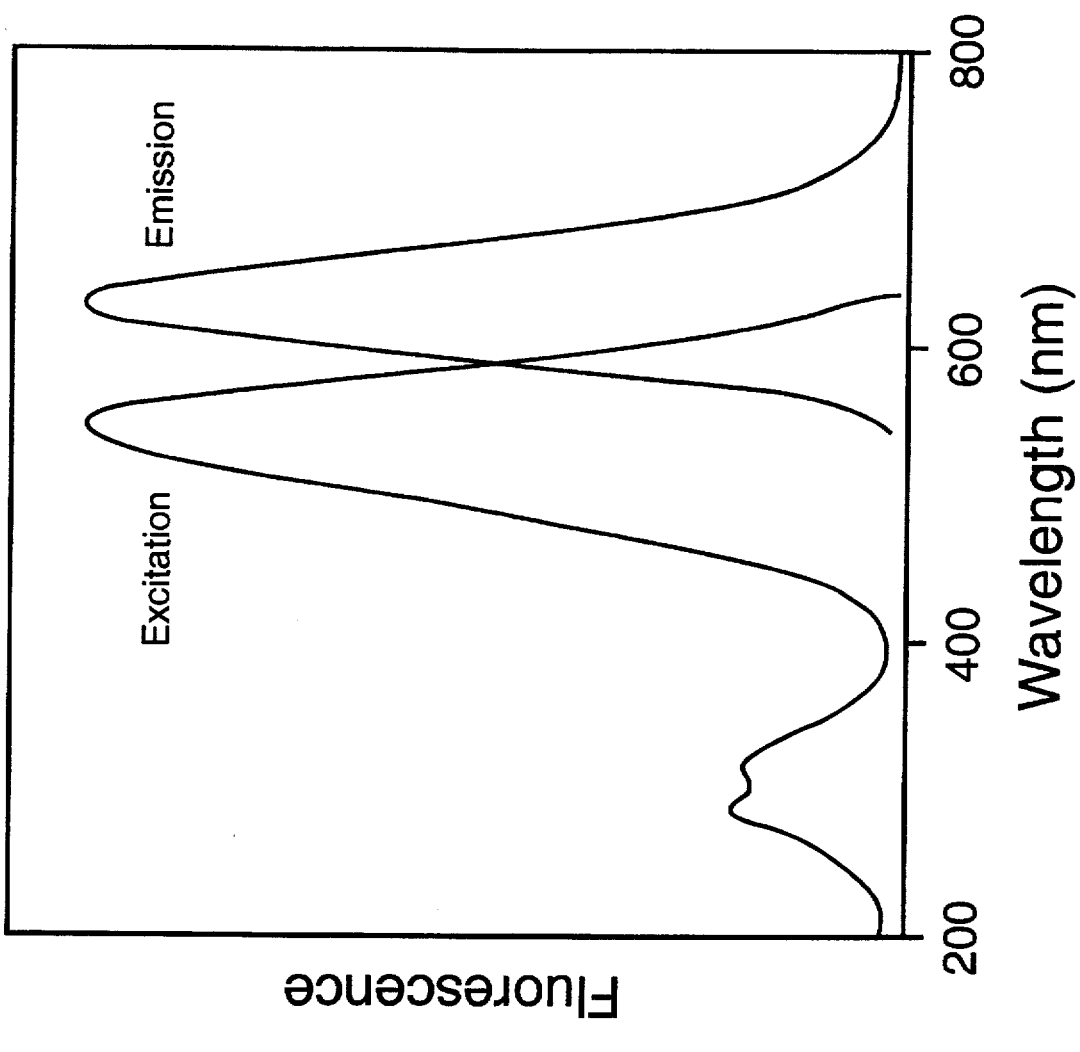
FIG. 1: Normalized excitation and emission spectra for Dye 801 in the presence of poly(amino acid). Spectra were obtained on a 1 μM solution of Dye 801 in the presence of 150 μg/mL bovine serum albumin (BSA) and 0.05% SDS in 10 mM Tris-HCl, pH 7.5, using a standard fluorometer.
Figure 2:
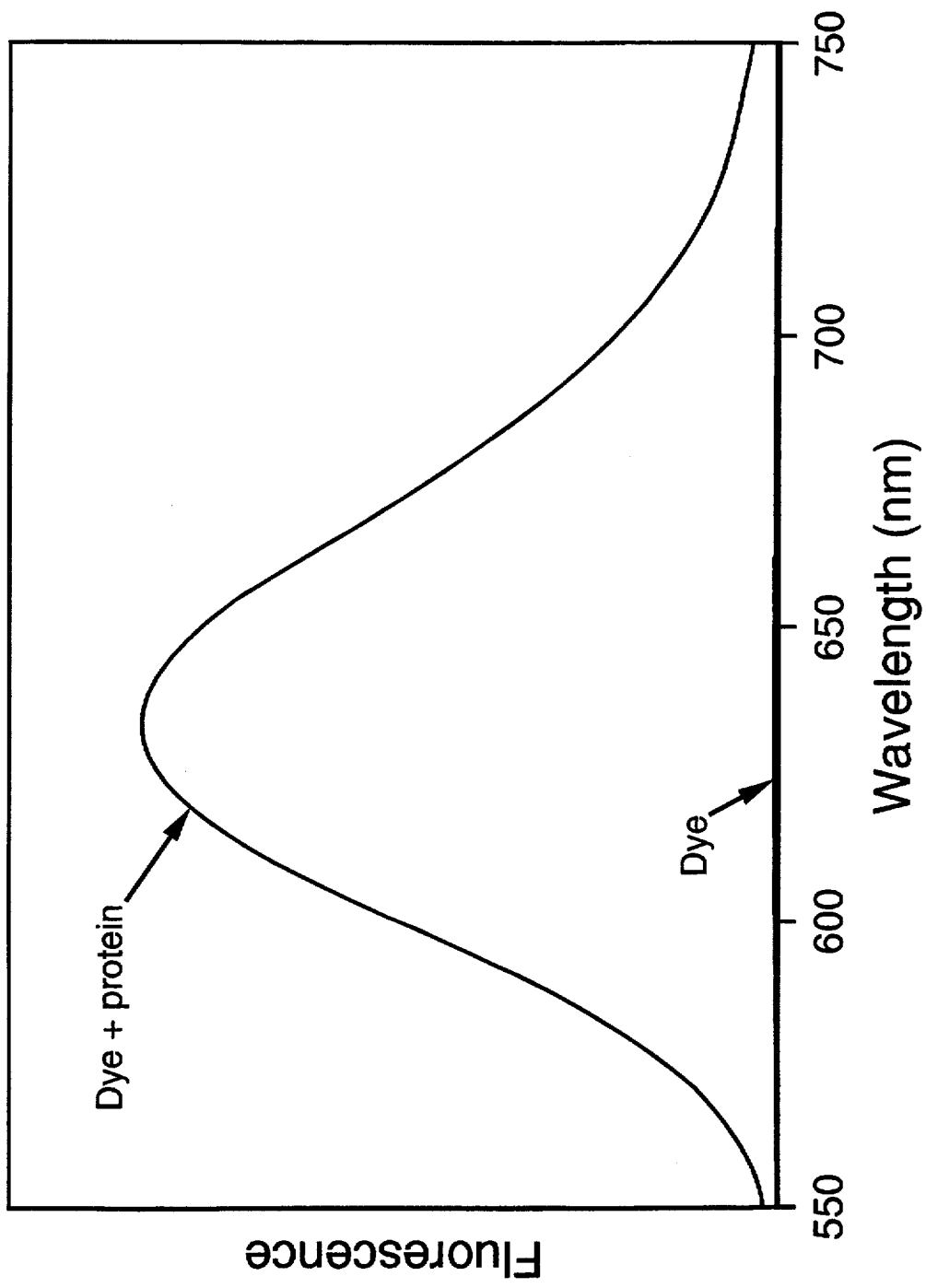
FIG. 2: Dye 801 fluorescence enhancement upon addition of poly(amino acid). Spectra were obtained using a 1 μM solution of Dye 801 and 0.05% SDS in 10 mM Tris-HCl, pH 7.5, in the absence and presence of 500 μg/mL bovine serum albumin (BSA), using a standard fluorometer.

The present invention relates to the use of merocyanine dyes for the staining and subsequent detection of poly(amino acids), including peptides, polypeptides, and proteins. The dyes of the invention associate with peptides and proteins either directly, or in the presence of a detergent, to yield both a strong colorimetric absorption and a strong fluorescence emission. Any poly(amino acid) thereby labeled is capable of being detected with great sensitivity either in solution, or on a solid or semisolid support.

Merocyanine dyes are a diverse group of dyes that comprise a quaternary nitrogen heterocycle linked to an electron pair-donating moiety by an alkylene or polyalkylene bridge. A wide variety of electron pair-donating groups are known that stabilize the formally positive charge of the quaternary nitrogen heterocycle by resonance. Suitable electron pair-donating groups include dialkylaminophenyl, dialkylaminonaphthyl, electron-rich heterocycles and acyclic moieties containing electron pair-donating groups.

The preferred merocyanine dyes of the present invention are described by the general formula

Q-B-M wherein Q is a quaternized nitrogen heterocycle where the quaternizing group is a TAIL group, B is a covalent bridge that is an ethenyl or polyethenyl bridging moiety, and M is an aromatic heterocyclic substituent or activated methylene substituent. Depiction of the instant dyes herein does not differentiate between cis and trans isomers; that is, isomers that differ only in the stereo chemistry of the ethylenyl moieties of B. It is to be understood that, except where expressly stated, the compounds implicitly include either the cis isomer, the trans isomer, or a mixture thereof.

The quaternized nitrogen heterocycle Q has the formula

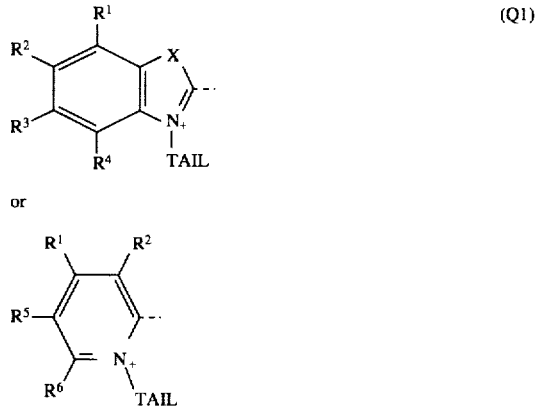

or or the formula

where the ring substituents $R^1$, $R^2$, $R^3$ and $R^4$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls. Alternatively, any two adjacent substituents of $R^1$, $R^2$, $R^3$ and $R^4$, when taken in combination, form a fused 6-membered aromatic ring that is optionally further substituted by Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls. The ring substituents $R^5$ and $R^6$ are optionally and independently H, Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls, or phenyl, where the phenyl ring is optionally further substituted by Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls. Alternatively, $R^5$ and $R^6$, when taken in combination, form a fused 6-membered aromatic ring (yielding a benzo-substituted pyridinium, or quinolinium moiety). The additional ring on the quinolinium that is thereby formed is optionally and independently substituted one or more times by Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls. Additionally, the quinolinium ring is optionally substituted by an additional fused 6-membered aromatic ring (yielding a naphtho-substituted pyridinium, or a benzoquinoline), that is also optionally and independently substituted one or more times by Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls. Typically, $R^5$ and $R^6$ are H, or form a substituted or unsubstituted benzo moiety. Preferably $R^5$ and $R^6$, taken in combination, form a fused 6-membered substituted or unsubstituted benzo moiety yielding a quinolinium ring system.

In the benzazole ring Q1, the ring fragment X is optionally —S—, —O—, —$NR^7$—, or —$CR^7R^8$—, wherein $R^7$ and $R^8$ are optionally and independently H, Cl, F, or $C_1$–$C_6$ alkyl; alternatively, $R^7$ and $R^8$ taken in combination complete a 5- or 6-membered saturated ring (—$(CH_2)_4$— or —$(CH_2)_5$—). Where X is —$CR^7R^8$—, $R^7$ and $R^8$ are typically $CH_3$. Preferably, X is O or S, more preferably X is S.

The quaternizing moiety, TAIL, is attached to the nitrogen atom of Q through a carbon atom and contains a total of 1–22 non-hydrogen atoms, wherein the non-hydrogen atoms are selected from the group consisting of C, O, N or S, such that within TAIL each heteroatom is separated from any adjacent heteroatoms by at least two carbon atoms. TAIL is composed of bonds that are selected from the group consisting of carbon-carbon bonds (C—C), ether bonds (C—O—C), thioether bonds (C—S—C) or amine bonds (C—NR—C). Any carbon atom in TAIL is optionally further substituted by hydroxy, carboxy, sulfo, amino, or ammonium. Any amine bond, amino or ammonium in TAIL is optionally substituted by $C_2$–$C_6$ alkyl that is optionally further substituted by hydroxy, carboxy, sulfo, amino, amino substituted by 1–2 $C_1$–$C_6$ alkyls or ammonium substituted by 1–3 $C_1$–$C_6$ alkyls. Alternatively, the nitrogen atoms of TAIL form either one or two saturated 5- or 6-membered rings in combination with other C or N atoms in TAIL, such that the resulting rings are pyrrolidines, piperidines, piperazines or morpholines.

In one preferred embodiment of the invention, the TAIL moiety includes at least one nitrogen heteroatom, preferably wherein the nitrogen atom is a dialkylamino or a trialkylammonium substituent, and where the alkyl substituents are methyl or ethyl. Preferably, TAIL, is —$CH_3$, or $CH_2CH_3$, or TAIL is a $C_3$–$C_{22}$ alkyl chain that is linear or branched, saturated or unsaturated, and that is optionally substituted one or more times by hydroxy, carboxy, sulfo, amino, amino substituted by 1–2 $C_1$–$C_6$ alkyls, or ammonium substituted by 1–3 $C_1$–$C_6$ alkyls. By "sulfo" is meant sulfonic acid (—$SO_3H$) or the common alkali metal salts of sulfonic acid. More preferably, TAIL is a $C_3$–$C_{12}$ alkyl chain that is linear and saturated, and substituted at its free terminus by hydroxy, carboxy, sulfo, amino, amino substituted by 1–2 $C_1$–$C_6$ alkyls, or ammonium substituted by 1–3 $C_1$–$C_6$ alkyls. Yet more preferably, the TAIL moiety is a $C_3$–$C_4$ alkyl that is substituted once by sulfo or carboxy.

The covalent bridge, B, has the formula —$(CR^7=CR^8)_n$—, where $R^7$ and $R^8$ have been defined previously. The subscript n has a value of 1–3, and determines how many conjugated alkenyl moieties are joined to form the bridge. The spectral properties of the resulting dye are highly dependent upon the length of the bridge moiety, with the excitation and emission wavelengths shifting to longer wavelengths with the addition of each alkenyl moiety. Typically, $R^7$ and $R^8$ are both H. Preferably n=1 or 2.

The moiety M has the formula

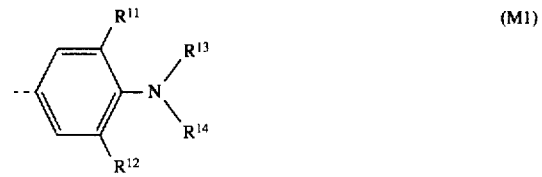

(M1)

or

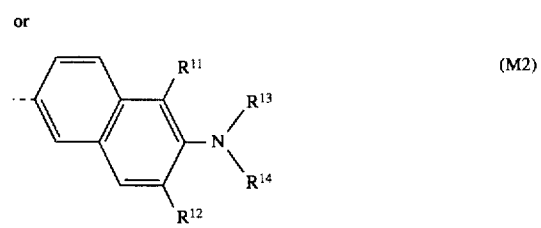

(M2)

where the ring substituents $R^{11}$ and $R^{12}$ are independently H, F, Cl, or —$CH_3$. Typically, $R^{11}$ and $R^{12}$ are H. The amino substituents $R^{13}$ and $R^{14}$ are independently $C_1$–$C_8$ alkyls that are linear, branched, saturated or unsaturated, and are optionally substituted one or more times by F, hydroxy or $C_1$–$C_6$ alkoxy. Alternatively, $R^{13}$ and $R^{14}$, when taken in combination, form a 5- or 6-membered saturated ring that optionally contains an oxygen heteroatom. In another embodiment of the dyes, $R^{11}$ taken in combination with $R^{13}$ and $R^{10}$ taken in combination with $R^{12}$ are independently —$(CH_2)_2$— or —$(CH_2)_3$—, forming 5- or 6-membered rings. Preferably $R^{13}$ and $R^{14}$ are each linear alkyls, which may be the same or different, each having 4–8 carbon atoms, more preferably each having 5 to 7 carbon atoms.

Alternatively, the electron pair-donating moiety M has the formula

(M3)

or

(M4)

or the formula

(M5)

Electron pair-donating moieties of formula M3 are acyclic, and are typically derivatives of malonic acid, cyanoacetic acid or malononitrile, while moieties of formula M4 or M5 are 5- and 6-membered heterocycles, respectively.

For all embodiments of M, Y is —OH, —SH,—$O^-$ or —$S^-$, preferably Y is —$O^-$ or —$S^-$, more preferably —$O^-$.

For the acyclic moiety M3, Z is —$OR^{15}$, —$SR^{15}$, —$N(R^{15})_2$, preferably —$OR^{15}$, where $R^{15}$ is H or $C_1$–$C_6$ alkyl. Where Z' is part of the heterocyclic rings of M4 and M5, Z' is one of —O—, —S—, or —$NR^{17}$—, where $R^{17}$ is H, $C_1$–$C_6$ alkyl, $C_1$–$C_6$ carboxyalkyl, phenyl or phenyl substituted by sulfo. Preferably Z' is —O— or —$NR^{17}$—. Preferably $R^{17}$ is alkyl, phenyl or phenyl substituted by sulfo. Where $R^{17}$ is phenyl substituted by sulfo, the sulfo is preferably at the para position of the phenyl ring.

W is a strong electron withdrawing group, and is one of CN, —(C=O)—$R^{16}$, or —(C=S)—$R^{16}$, preferably CN or —(C=O)—$R^{16}$, where $R^{16}$ is —$OR^{15}$, —$SR^{15}$, or —$N(R^{15})_2$, where $R^{15}$ has been defined above. In the 5-membered heterocyclic ring systems, W' is —O—, —S—, or —$NR^{17}$—, —(C=O)—, —(C=S)— or —(C=$NR^{17}$)—, where $R^{17}$ has been defined above. In the 6-membered heterocyclic ring systems, W" is —(C=O)—, —(C=S)— or —(C=$NR^{17}$)—, where $R^{17}$ has been defined above.

The 5-membered ring fragment $R^{18}$ is one of —O—, —S—, or —$NR^{16}$—. Alternatively, W' and $R^{18}$, when taken in combination and in that order, form the fragment —$CR^{17}$=N—. In another alternative, Z' and $R^{18}$, when taken in combination and in that order, form the fragment —$CR^{17}$=N—. For both of these alternatives, $R^{17}$ is preferably alkyl, phenyl or phenyl substituted by sulfo, as above.

The 6-membered ring fragment $R^{19}$ is either —O—, —S—, or —$NR^{17}$—, where $R^{17}$ has been defined previously. The additional 6-membered ring fragment, L, is either —(C=O)—, —(C=S)— or —(C=$NR^{17}$)—. Additionally, W" and $R^{19}$, when taken in combination and in that order, form the fragment —$CR^{17}$=N—.

In no embodiment of either the M4 or M5 moieties can the heterocycle contain ring segments that include O—O, S—S, O—S or N—N—N bonds.

Dyes that possess an electron pair-donating moiety having the formula M3, M4 or M5 are well known, and have been extensively described (Brooker et al., J. AM. CHEM. SOC. 73, 5326 (1951)). The description of these electron pair-donating moieties includes, but is not limited to, the specific dye fragments described below, where R is H, alkyl, carboxyalkyl, phenyl or sulfophenyl.

TABLE 1

Selected electron pair-donating moieties 5-pyrazolone
2-thiohydantoin
2,4-thiazolidinedione
2-imino-4-oxazolone TABLE 1-continued Selected electron pair-donating moieties 2-imino-4-thiazolidone
5(4H)-isoxazolone
2-thio-2,4-oxazolidinedione
barbituric acid
5-thiopyrazolone
2-thiobarbituric acid
5(4H)-oxazolone
3-thio-2,4-thiazolidinedione
cyanoacetate
malonate For all dyes of the invention, any net positive or negative charges possessed by the dye are balanced by a counterion or counterions. Where necessary, the counterion is depicted as Ψ and the polarity of the charge is indicated. Any of the common counterions currently used in conjunction with biomolecules is a suitable counterion for the dyes of the present invention. Examples of useful counterions for dyes having a net positive charge include, but are not limited to, chloride, bromide, iodide, sulfate, alkanesulfonate, arylsulfonate, phosphate, perchlorate, tetrafluoroborate, nitrate and anions of aromatic or aliphatic carboxylic acids. Preferred negative counterions are chloride, iodide, perchlorate and various sultanates. Examples of useful counterions for dyes having a net negative charge include, but are not limited to, alkali metal ions, alkaline earth metal ions, transition metal ions, ammonium or substituted ammonium ions.

Selected useful dyes for the method of the present invention are given in Table 2.

TABLE 2

Selected dyes of the present invention

| Dye no. | Dye Structure |
|---|---|
| 101 | $CH_3\overset{+}{-}N\langle pyridinium\rangle-CH=CH-\langle phenyl\rangle-N(C_{10}H_{21})_2$   $\Psi^-$ |
| 102 | $CH_3\overset{+}{-}N\langle quinolinium\rangle-CH=CH-\langle phenyl\rangle-N(CH_3)_2$   $\Psi^-$ |
| 103 | $(C_{22}H_{45})\overset{+}{-}N\langle pyridinium\rangle-CH=CH-\langle phenyl\rangle-N(CH_3)_2$   $\Psi^-$ |
| 104 | $CH_3\overset{+}{-}N\langle pyridinium\rangle-CH=CH-\langle phenyl\rangle-N\langle pyrrolidinyl\rangle$   $\Psi^-$ |
| 201 | $(C_2H_5)_3{}^+N-(CH_2)_3\overset{+}{-}N\langle pyridinium\rangle-(CH=CH)_2-\langle phenyl\rangle-N(C_2H_5)_2$   $\Psi^-$ |
| 301 | $^-O_3S-(CH_2)_3\overset{+}{-}N\langle pyridinium\rangle-CH=CH-\langle phenyl\rangle-N(C_2H_5)_2$ |
| 302 | $^-O_3S-(CH_2)_3\overset{+}{-}N\langle pyridinium\rangle-CH=CH-\langle phenyl\rangle-N(C_4H_9)_2$ |
| 303 | $^-O_3S-(CH_2)_3\overset{+}{-}N\langle pyridinium\rangle-CH=CH-\langle phenyl\rangle-N(C_5H_{11})_2$ |
| 304 | $^-O_3S-(CH_2)_3\overset{+}{-}N\langle pyridinium\rangle-CH=CH-\langle phenyl\rangle-N(C_6H_{13})_2$ |
| 305 | $^-O_3S-(CH_2)_3\overset{+}{-}N\langle pyridinium\rangle-CH=CH-\langle phenyl\rangle-N(C_{10}H_{21})_2$ |
| 306 | $^-O_3S-(CH_2)_4\overset{+}{-}N\langle pyridinium\rangle-CH=CH-\langle phenyl\rangle-N(C_5H_{11})_2$ |
| 307 | $^-O_3S-(CH_2)_4\overset{+}{-}N\langle pyridinium\rangle-CH=CH-\langle phenyl\rangle-N(C_6H_{13})_2$ |
| 308 | $^-O_3S-(CH_2)_4\overset{+}{-}N\langle pyridinium\rangle-CH=CH-\langle phenyl\rangle-N(C_8H_{17})_2$ |

TABLE 2-continued

Selected dyes of the present invention

| Dye no. | Dye Structure |
|---|---|
| 309 | $^-O_3S-(CH_2)_4-\overset{+}{N}\text{(pyridinium)}-(CH=CH)_2-\text{C}_6\text{H}_4-N(C_4H_9)_2$ |
| 310 | $^-O_3S-(CH_2)_4-\overset{+}{N}\text{(pyridinium)}-(CH=CH)_2-\text{C}_6\text{H}_4-N(C_5H_{11})_2$ |
| 311 | $^-O_3S-(CH_2)_4-\overset{+}{N}\text{(pyridinium)}-(CH=CH)_3-\text{C}_6\text{H}_4-N(C_4H_9)_2$ |
| 312 | $^-O_3S-(CH_2)_4-\overset{+}{N}\text{(pyridinium)}-CH=CH-\text{C}_6\text{H}_2(Cl)_2-N(C_6H_{13})_2$ |
| 313 | $^-O_3S-(CH_2)_4-\overset{+}{N}\text{(pyridinium)}-CH=CH-\text{C}_6\text{H}_4-N(CH_2(CF_2)_3CF_3)_2$ |
| 401 | $^-O_3S-(CH_2)_3-\overset{+}{N}\text{(pyridinium)}-CH=CH-\text{(naphthyl)}-N(C_4H_9)_2$ |
| 402 | $^-O_3S-(CH_2)_3-\overset{+}{N}\text{(pyridinium)}-CH=CH-\text{(naphthyl)}-N(C_8H_{17})_2$ |
| 501 | $^-O_3S-(CH_2)_4-\overset{+}{N}\text{(pyridinium)}-CH=CH-\text{(julolidyl)}$ |
| 601 | benzothiazolium with $(CH_2)_4-SO_3^-$ on N, $-CH=CH-C_6H_4-N(C_5H_{11})_2$ at 2-position |
| 701 | quinolinium with $(CH_2)_4-SO_3^-$ on $N^+$, $-CH=CH-C_6H_4-N(C_5H_{11})_2$ |

TABLE 2-continued

Selected dyes of the present invention

| Dye no. | Dye Structure |
|---|---|
| 702 | pyridinium-CH=CH-C$_6$H$_4$-N(C$_6$H$_{13}$)$_2$, N$^+$-(CH$_2$)$_5$-SO$_3^-$ |
| 801 | $^-$O$_3$S—(CH$_2$)$_4$—$^+$N(quinolinium)—CH=CH—C$_6$H$_4$—N(C$_5$H$_{11}$)$_2$ |
| 802 | $^-$O$_3$S—(CH$_2$)$_4$—$^+$N(quinolinium)—CH=CH—C$_6$H$_4$—N(C$_4$H$_9$)$_2$ |
| 803 | $^-$O$_3$S—(CH$_2$)$_4$—$^+$N(quinolinium)—CH=CH—C$_6$H$_4$—N(C$_6$H$_{13}$)$_2$ |
| 804 | (CH$_3$)$_2$N—(CH$_2$)$_3$—$^+$N(quinolinium)—CH=CH—C$_6$H$_4$—N(C$_5$H$_{11}$)$_2$, Ψ$^-$ |
| 805 | $^-$OOC—(CH$_2$)$_2$—$^+$N(quinolinium)—CH=CH—C$_6$H$_4$—N(C$_5$H$_{11}$)$_2$ |
| 806 | $^-$O$_3$S—(CH$_2$)$_4$—$^+$N(quinolinium, OCH$_3$ substituted)—CH=CH—C$_6$H$_4$—N(C$_5$H$_{11}$)$_2$ |
| 807 | $^-$O$_3$S—(CH$_2$)$_4$—$^+$N(quinolinium, N(C$_2$H$_5$)$_2$ substituted)—CH=CH—C$_6$H$_4$—N(C$_5$H$_{11}$)$_2$ |

TABLE 2-continued

Selected dyes of the present invention

| Dye no. | Dye Structure |
|---|---|
| 808 | Naphthoquinoline with $^-O_3S-(CH_2)_4-\overset{+}{N}$ substituent, linked by $-CH=CH-$ to phenyl-$N(C_5H_{11})_2$ |
| 809 | 2-Phenylquinoline with $^-O_3S-(CH_2)_4-\overset{+}{N}$ substituent, linked by $-CH=CH-$ to phenyl-$N(C_6H_{13})_2$ |
| 901 | Benzoxazole-$N^+(CH_2)_3-SO_3^-$, $-CH=CH-CH=CH-$ linked to thiobarbiturate with $C_4H_9$, $=S$, $C_4H_9$ substituents; $\Psi^+$ |
| 902 | Benzothiazole-$N^+(CH_2)_3-SO_3^-$, $-CH=CH-$ linked to pyrazolone with $CH_3$, azo-phenyl-$SO_3^-$; $\Psi^{2+}$ |
| 903 | Benzothiazole-$N^+(CH_2)_4-SO_3^-$, $-CH=CH-$ linked to thiohydantoin with $N-C_2H_5$, $=S$, $N$-phenyl; $\Psi^+$ |
| 904 | Quinoline with $^-O_3S-(CH_2)_4-\overset{+}{N}$ substituent, $-CH=CH-$ linked to rhodanine with $N-CH_2COOH$, $=S$; $\Psi^+$ |

TABLE 2-continued

Selected dyes of the present invention

| Dye no. | Dye Structure |
|---|---|
| 905 | 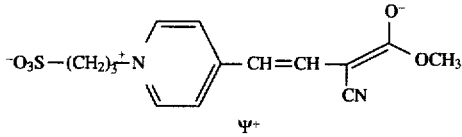 |
| 906 | 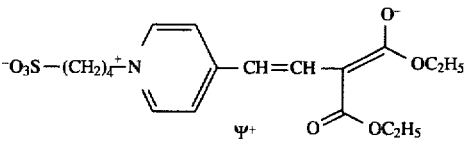 |

Merocyanine dyes, including styryl dyes, are widely known and have been extensively studied. Many of the dyes useful for the present invention are commercially available from Molecular Probes, Inc. (Eugene, Oreg.). However, a variety of methods exist for the synthesis of useful dyes for the present invention, as well as the preparation of useful analogs possessing modified substituents. For example, the preparation of those dyes having an M1 or M2 moiety is well-described by Grinvald et al. (supra) and Loew et al. (supra). Similarly, the preparation of those dyes having an M3, M4 or M5 moiety is described by Brooker et al. (supra).

The dyes of the invention generally possess four components: a) the quaternary nitrogen heterocycle (Q), b) the quaternizing moiety (TAIL), c) the bridging moiety, and d) the cyclic substituent (M) . Each portion is specifically described below.

a) The quaternary nitrogen heterocycle is generally a quaternized pyridine, quinoline or benzazole. However, merocyanines which contain addition fused rings, or wherein the pyridinium or quinolinium rings contain additional nitrogen atoms, such as azaquinolines or pyrimidines, are also useful for the present invention. To obtain the proper charge delocalization in pyridines and quinolines, the point of attachment of the double bond on the quaternary nitrogen is either at the carbon atom immediately adjacent to the quaternary nitrogen atoms (e.g. 2-pyridiniums) or at a position removed from the quaternary nitrogen atom by a carbon-carbon double bond (4-pyridiniums). Typically, all of the positions on the quaternary nitrogen heterocycle that are not attached to the bridge or TAIL are substituted by H, although quinolinium and benzazolium dyes that optionally contain additional substituents that are lower alkyl, lower alkoxy, halogens, amino or substituted amino may be used to further tune the spectral properties of the dye to match a desired excitation or emission wavelength.

b) The quaternizing moiety, herein referred to as TAIL, is typically obtained by quaternization of a methyl-substituted pyridine, quinoline or other nitrogen heterocycle by an alkylating agent that already contains other side chain substituents, or that is further reacted to yield the side chain substituents as described by Hildesheim (Grinvald et al. supra). In particular, quaternization with propane sultone or butane sultone is convenient and yields preferred dyes. Other particularly preferred dyes contain one or more amine or ammonia substituents in TAIL. These substituents are usually added either before or after synthesis of the initial merocyanine dye via an intermediate haloalkyl quaternized heterocycle. However, addition of TAIL is also achieved subsequent to initial dye synthesis, which usually requires an azastilbene or fused analog thereof, as described by Loew et al. (supra).

c) The bridging moiety is generally 1,2, 3 or more carbon-carbon double bonds. Typically the bridging moiety is 1 or 2 carbon-carbon double bonds. The addition of double bonds to the bridge generally shifts both the absorption and emission to longer wavelengths, the effect is also generally cumulative with the addition of multiple double bonds.

d) The electron pair-donating substituent is typically a substituted phenyl or naphthyl. More preferably the aromatic substituent is phenyl or naphthyl substituted by amino, alkylamino or dialkylamino. Generally, the dyes of the invention possess an aromatic substituent that is a dialkylaminophenyl or dialkylaminonaphthyl. These dyes are typically prepared by conversion of an aniline derivative that contains the desired $R^1$, $R^2$, $R^3$, and $R^4$ substituents to a benzaldehyde, cinnamaldehyde or pentadienal derivative using methods well known in the art. The aldehyde derivative is then condensed with a quaternized pyridinium, quinolinium or benzazolium salt to give the useful dye.

The electron pair-donating substituent is alternatively a heterocycle, provided that the substituents present on the heterocycle are able to stabilize the formal positive charge that is localized on the heterocycle nitrogen. Examples of this type of aromatic substituent include hydroxy- and amino-substituted heterocycles. The electron pair-donating substituent is alternatively an acyclic derivative of malonic acid, cyanoacetic acid or malononitrile.

Method of Use

The present invention utilizes the merocyanine dyes described above to stain poly(amino acids), followed by detection of the stained poly(amino acids) and optionally their quantification. By poly(amino acid) is meant any assemblage of multiple amino acids, which may be the same or different, that contain peptide linkages. The poly(amino acids) are stained by combining a sample mixture that is thought to contain poly(amino acids), with a staining mixture that comprises one or more merocyanine dyes to form a dye-poly(amino acid) complex that gives a detectable colorimetric or fluorescent optical response upon illumination. Additional steps are optionally and independently used, in any combination, to provide for separation or purification of the poly(amino acids), for enhancing the detection of the poly(amino acids), or for quantification of the poly(amino acids).

Sample Mixture

The sample mixture is a solid, paste, emulsion or solution that contains or is suspected to contain poly(amino acids). The sample mixture is an aqueous solution, typically prepared with water (e.g./br pure proteins) or aqueous buffer, or is combined with an aqueous solution in the course of labeling. By aqueous solution is meant a solution that is predominantly water and retains the solution characteristics of water. Where the solution contains solvents in addition to water, water is the predominant solvent.

The poly(amino acids) that are suitable for staining using this method include both synthetic and naturally occurring poly(amino acids), such as peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids. The poly(amino acids) are optionally relatively homogeneous or heterogeneous mixtures of poly(amino acids). In one aspect of the invention the poly(amino acids) are enzymes, antibodies, transcription factors, secreted proteins, structural proteins, or binding factors, or combinations thereof. The poly(amino acids) in the sample mixture are optionally covalently or non-covalently bound to a solid surface, such as a glass slide, multi-well plate, microtiter plate well, plastic pin or bead, or semiconductor material, or they are unbound. The staining of a poly(amino acid) that is bound to an analyte on a solid surface indicates the presence of the analyte as well as that of the poly(amino acid).

The poly(amino acids) are optionally unmodified, or have been treated with a reagent so as to enhance or decrease the mobility of the poly(amino acid) in an electrophoretic gel. Such reagents may modify poly(amino acids) by complexing with the peptide (to decrease migration), by cleaving selected peptide bonds (to increase migration of the resulting fragments), by changing the relative charge on the protein (as by phosphorylation or dephosphorylation) or by covalent coupling of a constituent such as occurs during glycosylation. The presence or interaction of such a reagent in the sample mixture is detected by the change in electrophoretic mobility of the treated poly(amino acids), relative to untreated poly(amino acids) having the same original composition, so that the distribution of the dye-poly(amino acid) complex indicates the presence of another analyte.

Although individual amino acids have been labeled using these merocyanine dyes, typically the poly(amino acids) in the sample mixture have a molecular weight greater than about 500 daltons. More typically the poly(amino acids) are more than 800 daltons. Smaller polymers of amino acids (in the <1000 dalton range) are generally difficult to separate from the detergent front on denaturing gels, and typically do not adhere to filter membranes, but are still readily detected in solution. There is no precise upper limit on the size of the poly(amino acids) that may be stained and detected, except that they can not be so bulky that they precipitate out of solution, which also depends in part on the relative hydrophobicity of the poly(amino acid). Furthermore, poly(amino acids) greater than about 200,000 daltons are generally not effectively resolved with current gel technology. The poly(amino acids) present optionally have essentially the same molecular weight or fall within a range of molecular weights. In one embodiment of the invention, the poly(amino acids) present are a mixture of poly(amino acids) of different molecular weights that are used as molecular weight standards. A typical such mixture contains equal mass quantities of myosin, β-galactosidase, phosphorylase B, bovine serum albumin, ovalbumin, carbonic anhydrase, trypsin inhibitor, lysozyme and aprotinin. The present invention also efficiently stains low molecular weight peptides, polypeptides and proteins, such as insulin, aprotinin, α-bungarotoxin, and a tetramer repeat of the RNA polymerase II C-terminal heptapeptide repeat.

Where the sample mixture is an aqueous solution, the poly(amino acids) of the sample mixture are typically present in a concentration of 10 ng/mL–50 µg/mL, more pretizrably in a concentration of 30 ng/mL–10 µg/mL, most preferably in a concentration of 50 ng/mL–5 µg/mL. Where the sample mixture is an electrophoretic gel, the poly(amino acids) of the sample mixture are typically present in a concentration of 1 ng/band–4 µg/band.

The poly(amino acids) are obtained from a variety of sources; such sources include biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids.

Depending on the source of the sample mixture, it optionally contains discrete biological ingredients other than the desired poly(amino acids), including poly(amino acids) other than those desired, amino acids, nucleic acids, carbohydrates, and lipids, which may or may not be removed in the course of, prior to, or after staining. In one aspect of the invention, the poly(amino acids) in the sample mixture are separated from each other or from other ingredients in the sample by mobility (e.g. electrophoretic gel or capillary) or by size (e.g. centrifugation, pelleting or density gradient), or by binding affinity (e.g. to a filter membrane) in the course of the method. In another aspect of the invention, the sample mixture thought to contain the poly(amino acids) has undergone separation. In yet another aspect of the invention, the poly(amino acids) are not separated. Although lipid assemblies such as intact or fragmented biological membranes (e.g. membranes of cells and organelles), liposomes, or detergent micelles, and other lipids are optionally present in the sample mixture; the presence of large amounts of lipids, particularly lipid assemblies, increases background labeling due to non-specific staining. For effective detection of labeled poly(amino acids), intact or fragmented biological membranes in the sample mixture are preferably removed, destroyed or dispersed prior to or in the course of labeling with this method. Typically treatment of the sample mixture by standard methods to remove some or all of such lipids, such as ammonium sulfate precipitation, solvent extraction or trichloroacetic acid precipitation is used. Alternatively or additionally, lipids are removed in the course of labeling the poly(amino acids) such as by electrophoretic separation or other separation techniques (e.g. centrifugation, including gradients), or are disrupted or dispersed below the concentration at which they assemble into micelles (critical micelle concentration) by mechanical means such as sonication. Naturally occurring lipids that are present below their critical micelie concentration are optionally used as a detergent for the purposes of the present invention. Typically, the sample mixture is essentially cell-free. This method is not effective for detecting proteins that remain in cells or are associated with biological membranes.

Staining mixture

To make a staining mixture to combine with the sample mixture, the selected dye is typically first dissolved in an organic solvent, such as DMSO, DMF or methanol, usually to a dye concentration of 1–10 mM. This concentrated stock solution is then generally diluted with an aqueous solution according to the assay being performed. Staining solutions can be stored and reused for months without signal loss. Acetic acid is optionally included in the staining mixture, typically to a concentration of 5%–7.5% acetic acid, e.g. to improve labeling of gels relative to that obtained for dyes in water. For staining polypeptides in solution, the dye is diluted into an aqueous solution, preferably a buffered solution, that optionally contains a detergent. For staining poly(amino acids) on gels or membranes, the dyes are diluted into water or buffer.

For visible color detection, dye concentrations in the staining mixture are typically between 1 $\mu$M and 100 $\mu$M, preferably between about 5 $\mu$M and about 20 $\mu$M; more preferably at least 10–15 $\mu$M or higher, although concentrations below or above these values also results in detectable staining for certain poly(amino acids). For fluorescence detection, dye concentrations are typically greater than 0.10 $\mu$M and less than 10 $\mu$M; preferably greater than about 0.50 $\mu$M and less than or equal to about 5 $\mu$M; more preferably 1–3 $\mu$M. Although concentrations below and above these values likewise result in detectable staining for certain poly(amino acids), depending on the sensitivity of the detection method, dye concentrations greater than about 10 $\mu$M generally lead to quenching of the fluorescence signal. The sensitivity for visible color detection is generally lower than that observed with fluorescence detection.

A particular dye is generally selected for a particular assay using one or more of the following criteria: sensitivity to poly(amino acids), dynamic range, photostability, staining time, and insensitivity to the presence of nucleic acids. The sensitivity and dynamic range of the dyes is determined using the procedures of Examples 1 and 7. Preferably, the dyes of the present invention have a sensitivity of 1–2 ng or less of poly(amino acid) per band in electrophoretic gels, or 10–30 ng or less of poly(amino acid) per mL of solution. The preferred dyes of the present invention have a dynamic range of about 3 or more orders of magnitude of poly(amino acid) concentration for solution assays.

The preferred dyes of the invention, in an aqueous solution in the absence of poly(amino acids), possess a quantum yield of less than 0.05, more preferably less than 0.01. The preferred dyes also, in an aqueous solution in combination with poly(amino acids), e,exhibit a fluorescence enhancement that is preferably greater than 100-fold, more preferably greater than 300-fold relative to the dyes in the absence of poly(amino acids). The preferred dyes of the present invention, when present in an aqueous solution that contains a detergent in an amount below its critical micelle concentration, possess an absorption maximum that is within 10 nm of 488 nm, 543 nm, 590 nm or 633 nm. 30. In one embodiment, the preferred dyes of the invention possess less than a full ionic charge at pH 7. In another embodiment, the preferred dyes of the invention are monocationic at pH 7. Finally, the preferred dyes of the invention have a molecular weight of 430–680 grams per mole.

Detergent

The present method of staining poly(amino acids) optionally includes the addition of a detergent. The detergent is optionally added simultaneously with or as part of the sample mixture or the staining mixture, or is added thereafter to the combined mixture as described below. The detergent is any amphiphilic surface active agent or surfactant that serves to coat the poly(amino acids), i.e. non-covalently associate with the poly(amino acid). Useful detergents include non-ionic, cationic, anionic, amphoteric and fluorinated surfactants. While there are a variety of detergents that are commercially available, including non-ionic, cationic, and anionic detergents, any detergent that is utilized in protein gel electrophoresis is a preferred detergent for the present invention. Typically, the detergent is an anionic detergent, preferably an alkyl sulfate or alkyl sulfonate salt. More preferably, the detergent is sodium dodecyl sulfate (SDS), sodium octadecyl sulfate, or sodium decyl sulfate. Most preferably, the detergent is sodium dodecyl sulfate.

The dyes of the invention typically stain micelles, even in the absence of poly(amino acids). It is therefore preferred that any detergent present in the sample mixture, staining mixture, or combined mixture be present below the critical micelle concentration (CMC) for that detergent, in order to avoid poly(amino acid)-free micelle formation. The CMC is a function of the detergent being used and the ionic strength of the solution. For SDS solutions at moderate ionic strength, the CMC is about 0.1% of the solution by weight. Where the concentration of SDS in the sample mixture is less than about 0.1%, the background fluorescence is typically lower than for sample mixtures containing higher concentrations of SDS. Typically, for pertaining the sample mixture before electrophoretic separation of denatured poly(amino acids) using SDS, the concentration of the detergent is about 1–5% by weight, more typically about 2%. Where the combined mixture is used for a solution assay, the concentration of SDS in the combined mixture is typically less than 1% by weight, preferably 0.05–0.1% by weight. For non-ionic detergents such as PLUTONIC and TRITON, the concentration of detergent in the combined mixture is preferably less than about 0.05% by weight.

Combined mixture

The staining mixture is combined with the sample mixture in such a way as to facilitate contact between any dye and any poly(amino acids) present in the combined mixture. Except for embodiments where non-denaturing gels are being used, optionally present in the combined mixture is a detergent that is added simultaneously with or as part of the sample mixture or the staining mixture, or is added thereafter to the combined mixture. Preferably, the detergent is combined with the sample mixture before the staining mixture is added.

The association of the dye or dyes in the staining mixture with the poly(amino acids) in the sample mixture forms a dye-poly(amino acid) complex, which complex optionally contains detergent molecules, as described above. In one aspect of the invention, the dye-poly(amino acid) complex consists essentially of poly(amino acids), and one or more merocyanine dyes, in particular, preferred embodiments of the dyes as described above. In another aspect of the invention, the dye-poly(amino acid) complex further comprises detergent molecules, such that the merocyanine dyes present in the complex interact non-covalently with either the poly(amino acid) or with said detergent molecules.

In one aspect of the invention, the combined mixture is an aqueous solution (e.g. Example 7). Typically such solution consists essentially of poly(amino acids), one or more merocyanine dyes, particularly the preferred embodiments described above, and a detergent in an aqueous mixture. Preferably, the aqueous solution is a buffered solution. The aqueous solution is optionally used as a separation medium, such as within a sedimentation gradient (e.g. a sucrose gradient) or when performing capillary electrophoresis. Although amino acids in aqueous solution are also stained by merocyanine dyes, such staining is less intense than that of poly(amino acids). The optical properties of representative dyes in combination with representative poly(amino acids) in solution are given in Table 3. The data in Table 3 are generated using a standard procedure so as to allow direct comparison of differing dyes. As a result, the procedure is not necessarily optimized for a given dye. Greater sensitivity or dynamic range is possible upon optimization.

In another aspect of practicing the invention, the merocyanine dyes optionally are used to prestain poly(amino acids) prior to separation; or are present as a component of the mobile phase during separation (e.g. Example 13). The techniques of prestaining or staining with the running buffer work for both gel and capillary electrophoresis. Alternatively, separated poly(amino acids) in electrophoretic gels are post-stained using the staining mixture, or are transferred to a filter membrane or blot or other solid or semi-solid matrix before being combined with the staining mixture (e.g. Examples 1, 2, 3, and 5). The present method is effective for both denaturing and non-denaturing gels. Denaturing gels optionally include a detergent such as SDS or other alkyl sulfonate (e.g. 0.05%–0.1% SDS). Typically, polyacrylamide or agarose gels are used for electrophoresis. Commonly used polyacrylamide gels include but are not limited to Tris-glycine, Tris-tricine, mini- or full-sized gels, generally possessing a stacking gel. Agarose gels include modified agaroses. Alternatively, the gel is an iso-electric focusing gel. In addition to polyacrylamide and agarose gels, suitable electrophoresis gels are optionally prepared using other polymers, such as HYDROLINK. Alternatively, the electrophoretic gel is a gradient gel. The sample mixture or combined mixture is optionally heated before being applied to denaturing gels. Useful electrophoretic gels for the present invention are either prepared according to standard procedures or are purchased commercially (e.g. Bio-Rad Laboratories, Hercules, Calif.; FMC Bioproducts, Rockland, Md.). The sensitivities of selected dyes of the present invention when used to post-stain electrophoretic gels are listed in Table 4.

In another embodiment of the invention, the present method is used to detect poly(amino acids) present in a two-dimensional electrophoretic gel. In another embodiment of the invention, the electrophoretic gel is used for gel-mobility-shift analysis, where a polyacrylamide or agarose gel is cast and run in a buffer optimized to preserve the specific protein/nucleic acid interaction of interest. In both embodiments, the staining mixture is optionally combined with the sample mixture at any stage point in the electrophoresis procedure, but the dyes are preferably either present in the running buffer or used following electrophoretic separation as a post-stain.

The data presented in Tables 3 and 4 are generated using standardized procedures so as to allow direct comparison of differing dyes. As a result, the procedures used are not necessarily optimized for a given dye. Greater sensitivity or dynamic range is possible upon optimization, for example as presented in Table 5 and in selected Examples. Optimized dye characteristics may vary from the results shown in Tables 3 and 4.

TABLE 3

Properties of selected dyes in solution assays

| Dye No. | Absorbence (nm)[1] | | Fluorescence (nm)[2] dye + protein | | Fluorescence Enhancement[3] | Dynamic Range Limits[4] (μg protein) | |
|---|---|---|---|---|---|---|---|
| | free dye | dye + protein | excitation | emission | | lower | upper |
| 101 | 448 | 447 | 469 | 583 | 1.1 | 10 | 10 |
| 102 | 509 | 508 | 526 | 624 | 2 | 0.05 | 5 |
| 104 | 463 | 468 | 469 | 570 | 12.7 | 0.05 | 5 |
| 106 | 440 | 437 | 448 | 578 | 1.1 | 50 | 50 |
| 201 | 480 | 507 | 494 | 635 | 142 | 0.05 | 10 |
| 301 | 473 | 474 | 473 | 576 | 23.5 | 0.5 | 25 |
| 302 | 479 | 476 | 469 | 576 | 188 | 0.05 | 5 |
| 303 | 475 | 476 | 472 | 569 | 363 | 0.05 | 5 |
| 304 | 464 | 473 | 470 | 569 | 533 | 0.05 | 5 |
| 305 | 465 | 465 | 471 | 568 | 12.3 | 0.5 | 0.5 |
| 306 | 472 | 472 | 469 | 567 | 307 | 0.05 | 5 |
| 307 | 461 | 472 | 469 | 569 | 443 | 0.05 | 5 |
| 308 | 458 | 470 | 470 | 568 | 202 | 0.05 | 5 |
| 309 | 507 | 507 | 483 | 629 | 283 | 0.05 | 5 |
| 310 | 507 | 507 | 483 | 628 | 356 | 0.05 | 5 |
| 311 | 479 | 508 | 504 | 669 | 158 | 0.25 | 5 |
| 401 | 472 | 476 | 470 | 611 | 679 | 0.25 | 5 |
| 402 | 455 | 467 | 472 | 597 | 20.2 | 0.05 | 1 |
| 501 | 506 | 506 | 496 | 589 | 76.2 | 0.25 | 10 |
| 601 | 471 | 472 | 545 | 584 | 154 | 0.05 | 10 |
| 701 | 508 | 513 | 526 | 594 | 534 | 0.25 | 10 |
| 801 | 538 | 543 | 547 | 631 | 1285 | 0.25 | 10 |
| 802 | 542 | 543 | 554 | 623 | 351 | 0.05 | 10 |
| 803 | 507 | 537 | 544 | 630 | 2238 | 0.25 | 10 |
| 901 | 506 | 506 | 560 | 570 | 66.2 | 2.5 | 50 |

[1]Absorbence maxima are determined using 1 μM dye + 0.05% SDS +/− 150 μg/mL BSA (bovine serum albumin) in a 2.0 mL volume using a UV-visible spectrophotometer.
[2]Fluorescence excitation and emission spectra are measured using 1 μM dye + 150 μg/mL BSA + 0.05% SDS in 2.0 mL volume with a standard fluorometer.

TABLE 3-continued

Properties of selected dyes in solution assays

| Dye No. | Absorbence (nm)[1] | | Fluorescence (nm)[2] dye + protein | | Fluorescence Enhancement[3] | Dynamic Range Limits[4] (μg protein) | |
|---|---|---|---|---|---|---|---|
| | free dye | dye + protein | excitation | emission | | lower | upper |

[3]Fluorescence enhancements are calculated using 1 μM dye +/− 500 μg/mL BSA in 2.0 mL in a standard fluorometer at fluorescence excitation and emission maxima.
[4]Dynamic range limits are determined by titrating a 1 μM solution of each dye with 0.05 to 50 μg protein in a 96 well microtiter plate in a 200 μL volume. Three protein solutions are titrated separately for each dye: lysozyme, BSA and a protein mixture that contains equal weight concentrations of IgG, avidin, streptavidin, cellulase and ovalbumin. Fluorescence is measured in a microtiter plate reader using an appropriate filter. The lower limit of detection is the amount of protein required to produce fluorescence 10% above the background fluorescence. The upper limit of the dynamic range is where the linearity of signal with respect to protein concentration starts to degrade. As the dynamic range tends to vary with different protein types, the upper limit is chosen for the limiting protein, or the protein type producing the signal saturation at the lowest concentration.

TABLE 4

Labeling sensitivity in gels of selected dyes[1]

| Dye No. | Color[2] | Sensitivity[3] (ng/band) | Background Staining |
|---|---|---|---|
| Coomassie Brilliant Blue | blue* | 30–60 (low) | very high: requires destaining |
| Nile red | red/orange* | 30–60 (low) | low/med |
| Silver staining | tan to black* | variable 2–10 (high) | varies, low to very high even with destaining |
| 101 | faint greenish | low | med |
| 102 | light orange | med | med |
| 103 | red/orange | low | low/med |
| 104 | yellow | med | low/med |
| 201 | red/orange | med | low/med |
| 301 | barely visible | low | low |
| 302 | greenish/pink | low | low |
| 303 | pink/yellow to orange | med | med |
| 304 | bright orange | high | low/med |
| 305 | light orange | low | med |
| 306 | orange | med | low |
| 307 | bright orange | high | low/med |
| 308 | orange | high | med |
| 309 | pink/orange | med | low |
| 310 | red/orange | high | low/med |
| 311 | fight orange | low | low/med |
| 401 | orange | med | med |
| 402 | red/orange | high | low |
| 501 | orange | med | low/med |
| 601 | red/orange | high | low |
| 701 | red/orange | high | low |
| 801 | red | high | low |
| 803 | red | high | low |
| 802 | red | high | low |
| 901 | orange | med | med/high |

[1]All electrophoretic gels are SDS acrylamide mini-gels (Bio-Rad Laboratories, Hercules, CA)
[2]Color refers to the color of the fluorescence emission of the stained protein bands, except where marked with * where color refers to colorimetric appearance under white light.
[3]Sensitivity refers to the lower limit of protein detection, per band, using a 4X dilution series of BSA (using the procedure of Example 1). The sensitivity is defined to be the band containing the smallest amount of protein that is easily detectable by eye in a black and white Polaroid photograph taken at an optimal exposure (the exposure times varied and were optimized for each dye). "Low" sensitivity means a detection limit comparable to that found with CBB and Nile Red; "high" sensitivity means a detection limit comparable to that found with silver staining, "medium" sensitivity is intermediate between the two ranges.

The sensitivity protein detection of the present method was compared to that of silver staining and CBB staining for electrophoretic gels containing a variety of poly(amino acids) having a range of molecular weights. The results are shown in Table 5, below.

TABLE 5

Sensitivity of detection as a function of poly(amino acid) composition

| Protein | Molecular Weight (Daltons) | Sensitivity Dye 304 (ng) | Sensitivity Silver Staining (ng) | Sensitivity CBB Staining (ng) |
|---|---|---|---|---|
| myosin | 200,000 | 1 | 1 | 8–16 |
| β-galactosidase | 116,250 | 1 | 2–4 | 8–16 |
| phosphorylase B | 97,400 | 2–4 | 1 | 30–60 |
| fructose-6-phosphate kinase | 85,200 | 1–2 | 2–4 | 31–62 |
| bovine serum albumin | 66,200 | 2–4 | 2–4 | 16–30 |
| bovine cytochrome C oxidase (COX) subunit I | 56,900 | 1–2 | 26–52 | 105 |
| glutamate dehydrogenase | 55,400 | 1–2 | 2–4 | 16 |
| IgG (heavy chain) | 50,000 | 2 | 4 | 34–69 |
| ovalbumin | 45,000 | 1–2 | 1–2 | 16–30 |
| Protein A | 41,000 | 1 | 1–2 | 16 |

TABLE 5-continued

Sensitivity of detection as a function of poly(amino acid) composition

| Protein | Molecular Weight (Daltons) | Sensitivity Dye 304 (ng) | Sensitivity Silver Staining (ng) | Sensitivity CBB Staining (ng) |
|---|---|---|---|---|
| aldolase | 39,200 | 1–2 | 1 | 31–62 |
| carbonic anhydrase | 31,000 | 2 | 4–8 | 16–30 |
| COX subunit II | 29,900 | 1–2 | 2–4 | 27–54 |
| triose phosphate isoenerase | 26,600 | 1 | 1 | 16–31 |
| COX subunit III | 26,000 | 0.8 | 0.8–1.5 | 48 |
| Protein G | 26,000 | 2 | 16 | 32–64 |
| IgG (light chain) | 25,000 | 14 | 56 | 166 |
| soybean trypsin inhibitor | 21,500 | 1–2 | 2–4 | 16–30 |
| histone H1 | 20,000 | 10 | 80 | 80–160 |
| β-bungarotoxin subunit | 20,000 | 1.25–2.5 | 1.25 | 41 |
| COX subunit IV | 17,100 | 0.5–1 | 4–8 | 16–32 |
| avidin | 4 × 16,500 | 2 | 2–4 | 16 |
| streptavidin | 4 × 15,000 | 2 | 16 | 32–64 |
| histone H3 | 15,700 | 7.5 | 15 | 30–60 |
| NEUTRALITE avidin | 15,000 | 1–2 | 62 | 62 |
| lysozyme | 14,400 | 1–2 | 4 | 16–30 |
| histone H2A/H2B | 13,700 | 7 | 14–27 | 54 |
| pancreatic RNase A | 13,700 | 4–8 | 16–30 | 125 |
| COX subunit Va | 12,400 | 1 | 45 | 16–32 |
| histone H4 | 11,200 | 3 | 22–45 | 45 |
| COX subunit Vb | 10,700 | 1 | 4–8 | 16–32 |
| COX subunit VIa | 9,400 | 1 | 4–8 | 16–32 |
| α-bungarotoxin | 8,000 | 4–8 | 2–4 | 31–62 |
| β-bungarotoxin subunit | 7,000 | 3–6 | — | 175–350 |
| aprotinin | 6,500 | 2 | 4–8 | 16–30 |
| human insulin | 6,000 | 8 | 8 | 125–250 |

Using merocyanines dyes according to the present invention, destaining of stained gels is generally not necessary for either colorimetric or fluorescent detection of proteins, although at very high concentrations of dye, destaining is optionally used to improve visible color detection in gels. Stained gels are optionally washed briefly after staining to prevent transfer of dye to other surfaces. Where the staining mixture is the running buffer for an electrophoretic gel, however, destaining is recommended (e.g. with 7.5% acetic acid). The duration of staining is such that stained gels can be photographed as much as a few days after staining without significant loss of signal. If the signal is photobleached, gels can simply be restained as described above and the signal is restored.

Electrophoretic gels stained according to the method of the invention can subsequently be dried onto filter paper or between plastic sheets, using standard procedures. However, although the colored signal is extremely stable to drying, sensitivity of the fluorescent signal decreases upon drying. In addition, most plastics are not ultra-violet transparent, so that although visible bands remain in the gel, they can no longer be excited using ultra-violet illumination. However, both colorimetric and fluorescent signals in such bands can be detected using visible light sources.

Additional reagents

The method of the present invention optionally further comprises the addition of an additional reagent to the sample poly(amino acids). One or more additional reagents are optionally combined, simultaneously or sequentially, with the sample mixture, the staining mixture, or the combined mixture. An additional reagent is optionally a detection reagent that colocalizes with poly(amino acids) in general or with specific poly(amino acids) to enhance the detection thereof by the method of the present invention. Or, the additional reagent is a detection reagent designed to interact with a specific portion of the sample mixture, so as to probe for a specific component of the sample mixture, where spatial coincidence of merocyanine dyes and the detection reagent indicates that the additional reagent is also associated with the poly(amino acids).

For all embodiments, the additional reagent also incorporates a means for producing a detectable response. A detectable response means a change in, or occurrence of, a parameter in a test system which is capable of being perceived, either by direct observation or instrumentally, and which is a function of the presence of a specifically targeted member of a specific binding pair in a sample. Such detectable responses include the change in, or appearance of, color, fluorescence, reflectance, pH, chemiluminescence, infrared spectra, magnetic properties, radioactivity, light scattering, x-ray scattering, or an electron-rich substrate. Appropriate labels to provide a detectable response include, but are not limited to, a visible or fluorescent dye, an enzyme substrate that produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine). The detectable label of the additional reagent is detected simultaneously or sequentially with the optical signal of the stains of the present invention.

In one embodiment of the invention, one or more additional merocyanine dyes, including preferred embodiments described above, are the additional reagent(s). The merocyanine dyes optionally have overlapping spectral characteristics such that energy transfer occurs between the dyes in association with the poly(amino acids), resulting in labeled poly(amino acids) that exhibit an extended Stokes shift. Alternatively, the additional dye(s) colocalize with the first dye such that the labeling of some or all poly(amino acids) exhibits fluorescence quenching. Alternatively, the additional reagent is another protein stain (such as CBB or silver stain) such that labeling of the poly(amino acids) is enhanced by the colocalization of staining.

Other useful additional reagents are fluorescent nucleic acid stains. A variety of appropriate nucleic acid stains are known in the art, including but not limited to, Thiazole Orange, ethidium homodimer, ethidium bromide, propidium iodide, Hoechst 33258, and DAPI. Additional useful nucleic acid stains are described in the international applications WO 93/06482, DIMERS OF UNSYMMETRICAL CYANINE DYES (published Apr. 1, 1993) or WO 94/24213, CYCLIC SUBSTITUTED UNSYMMETRICAL CYANINE DYES (published Oct. 27, 1994); U.S. Pat. No. 5,321,130 to Yue et al., 1994; or U.S. Pat. No. 5,410,030 DIMERS OF UNSYMMETRICAL CYANINE DYES CONTAINING PYRIDINIUM Moieties to Yue et al., 1995. The use of an appropriate nucleic acid stain in conjunction with the dyes of the present invention can be selected to allow simultaneous or sequential observation of poly(amino acids) and nucleic acids such as DNA and RNA.

In one embodiment, the additional reagent comprises a member of a specific binding pair having a detectable label. Representative specific binding pairs are shown, in Table 6.

TABLE 6

Representative specific binding pairs

| | |
|---|---|
| enzyme | enzyme substrate |
| antigen | antibody |
| biotin | avidin (or streptavidin) |
| IgG* | protein A or protein G |
| carbohydrate | lectin |

*IgG is an immnunoglobulin

The additional reagent may be used in conjunction with enzyme conjugates to localize the detectable response of the reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

Alternatively, the additional reagent is optionally not a detection reagent but interacts with the poly(amino acids) in the sample so as to enhance or decrease mobility in an electrophoretic gel, as by complexing with the peptide (to decrease migration) or by cleaving some peptide bonds (to increase migration of the resulting fragments), or by changing the relative charge on the protein (e.g. by phosphorylation or dephosphorylation) or by covalent coupling of a constituent such as occurs during glycosylation. The presence or interaction of such reagent in the sample mixture is detected by the change in electrophoretic mobility of the sample mixture with and without such additional reagent.

Illumination and Observation

After addition of the dye to the sample, the sample is illuminated by a light source capable of exciting the dye-poly(amino acids) complex. Typically, the sample is excited by a light source capable of producing light at or near the wavelength of maximum absorption of the dye-poly(amino acid) complex, such as an ultraviolet or visible wavelength emission lamp, an arc lamp, a laser, or even sunlight or ordinary room light. Typically, ultraviolet excitation of the dyes occurs at 254–370 nm, while visible excitation occurs at 490–550 nm. Preferably the sample is excited with a wavelength within 20 nm of the maximum absorption of the dye-poly(amino acid) complex. Although excitation by a source more appropriate to the maximum absorption band of the dye-poly(amino acid) complex results in higher sensitivity, the equipment commonly available for excitation of fluorescent samples can be used to excite the stains of the present invention. Selected equipment that is useful for illuminating the dye-poly(amino acid) complex includes, but is not limited to, ultraviolet trans-illuminators, ultraviolet epi-illuminators, hand-held ultraviolet lamps, mercury arc lamps, xenon lamps, argon lasers, and YAG lasers. These illumination sources are optionally integrated into laser scanners, fluorescence microtiter plate readers, standard or mini fluorometers, gel readers, or chromatographic detectors.

Preferably, the dye-poly(amino acid) complexes of the present invention possess an absorption maximum between 480 and 650 nm, more preferably between 488 and 550 nm. More preferably, the dyes of the present invention are selected such that the absorption maximum of the resulting dye-poly(amino acid) complex matches the wavelength of a laser illumination source. Typically such complexes have absorption maxima within 10 nm of 488 nm, 514 nm, 543 nm, 590 nm or 633 nm. Also preferably, the complexes of the present invention excite efficiently in the ultraviolet wavelength range, more preferably at or near 300 nm The detectable optical response of the dye-poly(amino acid) complex in response to illumination is detected qualitatively, or optionally quantitatively. The detectable optical response of the dye-poly(amino acid) complex is an absorption of visible light (colorimetric response), or is a fluorescence emission (fluorescence response), or both.

The optical response is typically detected by means that include visual inspection, CCD cameras, video cameras, photographic film, or the use of currently used instrumentation such as laser scanning devices, fluorometers, photodiodes, quantum counters, epifluorescence microscopes, scanning microscopes, flow cytometers, fluorescence microtiter plate readers, or by means for amplifying the signal such as photomultiplier tubes. When recording the optical response of electrophoretic gels, the use of POLAROID film results in enhanced sensitivity of signal versus purely visual observation. The dye of the invention can be selected to have emission bands that match commercially available filter sets such as those for fluorescein or those used for detecting multiple fluorophores, which possess several excitation and emission bands. The sensitivity of detection is improved by use of techniques that permit separation of the poly(amino acids) on very thin gels or in microtube capillaries. The detection limits are also improved if the medium is illuminated by a stronger light such as a laser or detected with a more sensitive detector. The high Stokes shifts of the dyes of the present invention result in an excellent signal-to-noise ratio by decreasing the contribution of scattered light and endogenous fluorescence to the background.

A detectable change in the fluorescence properties of the dye-poly(amino acid) complex (detectable optical response) is optionally used to identify the presence of polypeptides in the test sample. Alternatively, the detectable optical response is quantified and used to measure the concentration of the poly(amino acid) in the test sample mixture. Quantification is typically performed by comparison of the optical response to a prepared standard or to a calibration curve. Typically, the measured optical response is compared with that obtained from a standard dilution of a known concentration of a poly(amino acid) or poly(amino acid) mixture, either in a fluorometer, in an electrophoretic gel, or on a membrane. Generally a standard curve must be prepared whenever an accurate measurement is desired. Alternatively, the standard curve is generated by comparison with a reference dye or dyed particle that has been standardized versus the target dye-poly(ammo acid) complex.

In one embodiment of the invention, the colorimetric or fluorescence properties of the prestained dye-poly(amino acid) complex are used to detect and/or quantify polypeptide bands in an electrophoresis gel. If a suitably visible light-transparent electrophoresis apparatus is used, the polypeptide bands in the gel can be observed visually or scanned instrumentally while the gel is within the electrophoresis apparatus, thereby making analysis faster and more economical.

Stained electrophoretic gels are used to analyze the composition of complex sample mixtures and additionally to determine the relative amount of a particular poly(anaino acid) in such mixtures. Stained gels are also used to estimate the purity of isolated proteins and to determine the degree of proteolytic degradation of poly(amino acids) in the sample mixture. In addition, electrophoretic mobility is optionally used to provide a measure of the size of uncharacterized poly(amino acids) and to analyze subunit composition for multi-subunit complexes, as well as to determine the stoichiometry for subunits bound in such complexes.

Due to the simplicity of use of the instant dyes, said dyes are particularly useful in the formulation of a kit for the labeling of poly(amino acids), comprising one or more merocyanine dyes (preferably in a stock solution) and instructions for the use of the dye to stain or detect peptides, polypeptides and/or proteins.

In another embodiment of the invention, the sample mixture and staining mixtures are applied, either simultaneously or sequentially to a solid or semi-solid support, the resulting color or fluorescence of which is then compared to a calibrated standard to determine the presence, and optionally the concentration, of poly(amino acid) present in the sample mixture. The support, dye solution, calibration standard and instructions for use, in combination, comprise a "dipstick" protein assay kit, allowing the rapid and convenient determination of protein concentration.

The examples below are given so as to illustrate the practice of this invention. They are not intended to limit or define the entire scope of this invention.

EXAMPLES

Example 1

Detection of proteins in sodium dodecyl sulfate (SDS)-polyacrylamide gels:

The pure protein or mixture of proteins of interest is prepared in Loading Buffer (50 mM Tris-HCl, pH 6.8, 2% SDS, 10% glycerol, and 0.015% bromophenol blue). Dithiothreitol is added to each sample, to a final concentration of 0.1M. The samples are heated for 4–5 minutes at 90°–95° C. and loaded onto a 15% Tris-glycine polyacrylamide minior full-sized gel containing 0.05%–0.1% SDS, with a 4% stacking gel. The gel is electrophoresed under standard conditions, in a standard Tris-glycine buffer containing 0.05%–0.1% SDS. The resulting gel is transferred to a small staining dish containing a 1–3 μM solution of Dye 304 in 7.5% acetic acid (in water). The staining solution is then covered with foil to protect it from room light and gently agitated for 45 minutes-1 hour. After 10 minutes, the protein bands are readily apparent, but sensitivity improves over about 30–40 minutes. The gel is then removed from the staining dish, rinsed briefly in 7.5% acetic acid and transferred directly to a UV-transilluminator. The gel, with the stained protein bands is photographed using 300 nm transillumination and black and white POLAROID 667 print film with a Wratten 9 gelatin filter. The stained bands appear visually as brightly fluorescent orange bands. Proteins appear as white bands on a grey to black background in the POLAROLD photograph. Alternatively, the stained gel is examined visually under normal room lights. The stained bands appear as orange bands.

Although Dye 304 is used in this procedure, a variety of other dyes of the invention are useful as electrophoretic gel stains (See Table 3), yielding stained gels that possess bands having visible coloring from yellow to purple and fluorescence emission from green to red.

Example 2

Detection of proteins in non-denaturing polyacrylamide gels:

A dilution series of the desired protein is prepared in Native Gel Loading Buffer (125 mM Tris-HCl, pH 6.8, 10% glycerol and 0.015% bromophenol blue). The samples are loaded onto a Tris-HCl non-denaturing polyacrylamide gel, and the gel is electrophoresed under standard conditions. The electrophoresed gel is stained and photographed as described in Example 1. Staining sensitivity under these conditions is typically somewhat protein-selective.

Example 3

Detection of peptides in Tris-Tricine gels:

A dilution series of a short peptide is prepared in Loading Buffer. To each sample dithiothreitol is added to a final concentration of 0.1M and the samples are heated for 4–5 minutes at 90°–95° C. and loaded onto 16.5% Tris-tricine gel. The gel is electrophoresed under standard conditions. The gel is then stained and the resulting protein bands are visualized as described in Example 1. Polypeptides as small as 20 amino acids are readily detected using this method. In addition, peptides such as a tetramer of the heptapeptide repeat found at the C-terminus of eukaryotic RNA polymerase II, tryptic peptides of trypsin and the small subtrait of β-bungarotoxin, which are not stained with either CBB or silver staining are readily detectable.

Example 4

Detection of proteins in 2-dimensional gels:

A mouse cytosolic extract (i.e., a whole cell lysate) is prepared and separated on a 2-dimensional gel under standard conditions. The gel is stained and visualized as described in Example 1 above. An identical gel is stained in parallel with silver using a commercially available kit (Bio-Rad, Hercules, Calif.). The gel stained using the method of the present invention exhibits more protein spots than the silver stained gel, indicating that the dyes of the present invention yield less protein-selective staining than silver staining. In addition, the intensity of the signal obtained with the instant method is more directly proportional to protein concentration than is the signal obtained with silver staining.

The sensitivity of staining using the dyes of the present invention is particularly superior to that of silver staining for detection of low molecular weight protein (Table 3).

Example 5

Detection of proteins on filter membranes following dot-blotting or Western transfer:

The protein of interest is diluted in TBS (20 mM Tris-HCl, pH 7.5, 500 mM NaCl), then applied directly to a nylon or nitrocellulose filter membrane. The membrane is washed once with TBS, then incubated with a solution containing 2 µM Dye 803 in 7.5% acetic acid or TBS. Alternatively, the proteins are first separated by gel electrophoresis and transferred to a nylon or nitrocellulose filter membrane using standard procedures. The blot is then stained as described above. The blot is illuminated with 300–365 nm light and protein spots or bands appear as fluorescent spots or bands. Blots are photographed as described above in Example 1. When photographed, stained proteins appear as faint white spots or white bands on the POLAROID image. Staining under these conditions is somewhat protein selective. Proteins are optionally detected using laser illumination sources.

Example 6

Western blotting of stained proteins:

A dilution series of the bovine heart cytochrome oxidase complex (COX) is prepared in water. Samples are loaded onto a 12% polyacrylamide gel and the gel is electrophoresed under standard conditions. The resulting gel is cut in half with a razor blade, then one half is stained with Dye 801 in transfer buffer (20% MeOH, 25 mM Tris-glycine, pH 8.3, 192 mM glycine) and visualized as described in Example 1 above. The stained proteins are then transferred from both halves of the gel to a filter membrane via electrophoretic transfer, according to standard methods. The blot is blocked, probed with mouse monoclonal antibodies directed against specific COX subunits, and the resulting signals are visualized using nitroblue tetrazoliuna in combination with 5-bromo-4-chloro-3-indolyl phosphate, using standard procedures. The two halves of the blot show equal sensitivity for detection of the COX subunits. This result indicates that staining proteins with the dyes of the present invention does not interfere with later immunological detection.

Example 7

Figure 3:
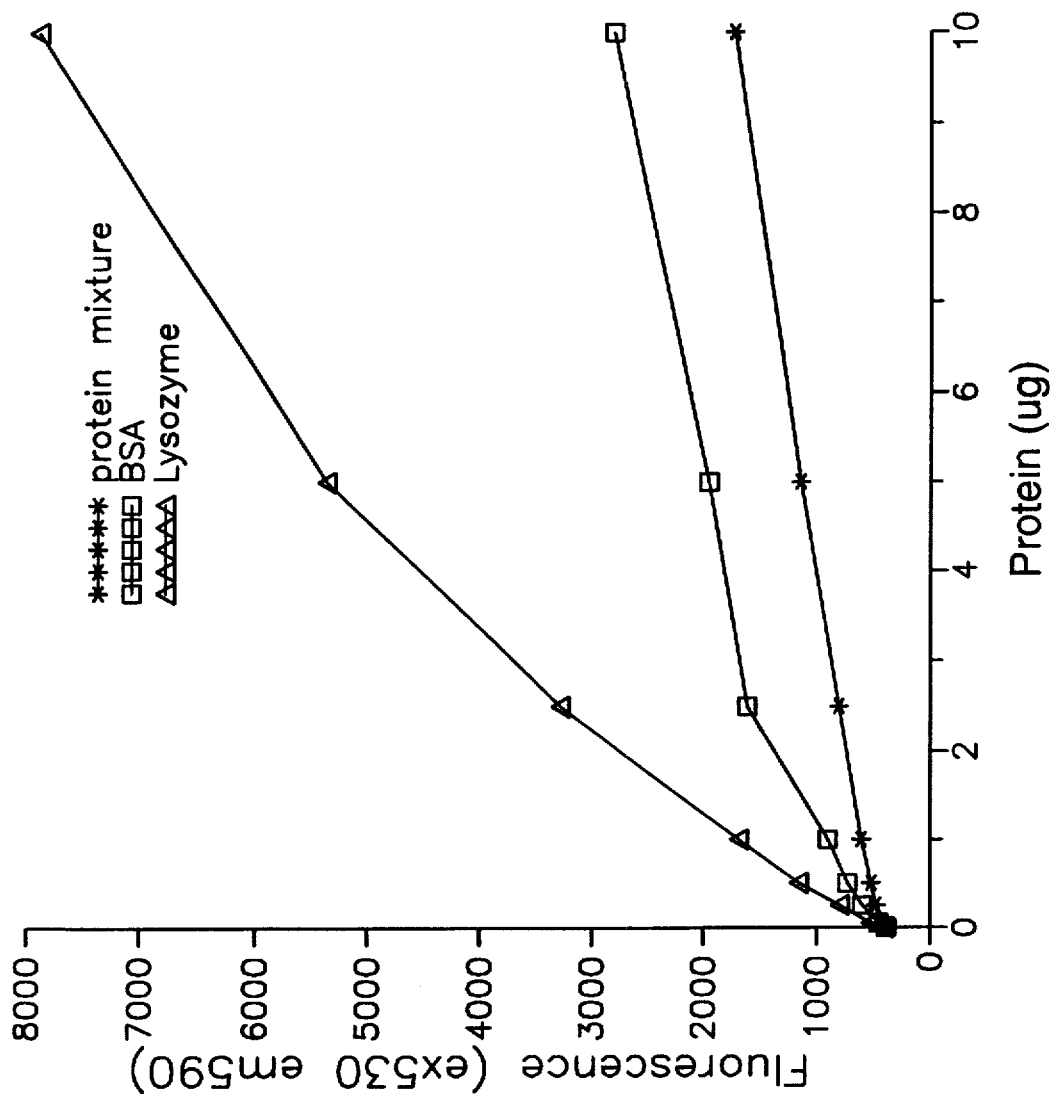
FIG. 3: Correlation between poly(amino acid) concentration and fluorescence emission for Dye 601 in a solution assay. The plot was prepared as described in Table 2, note 4, using excitation at 530 nm and recording the fluorescence emission at 590 nm
Figure 4:
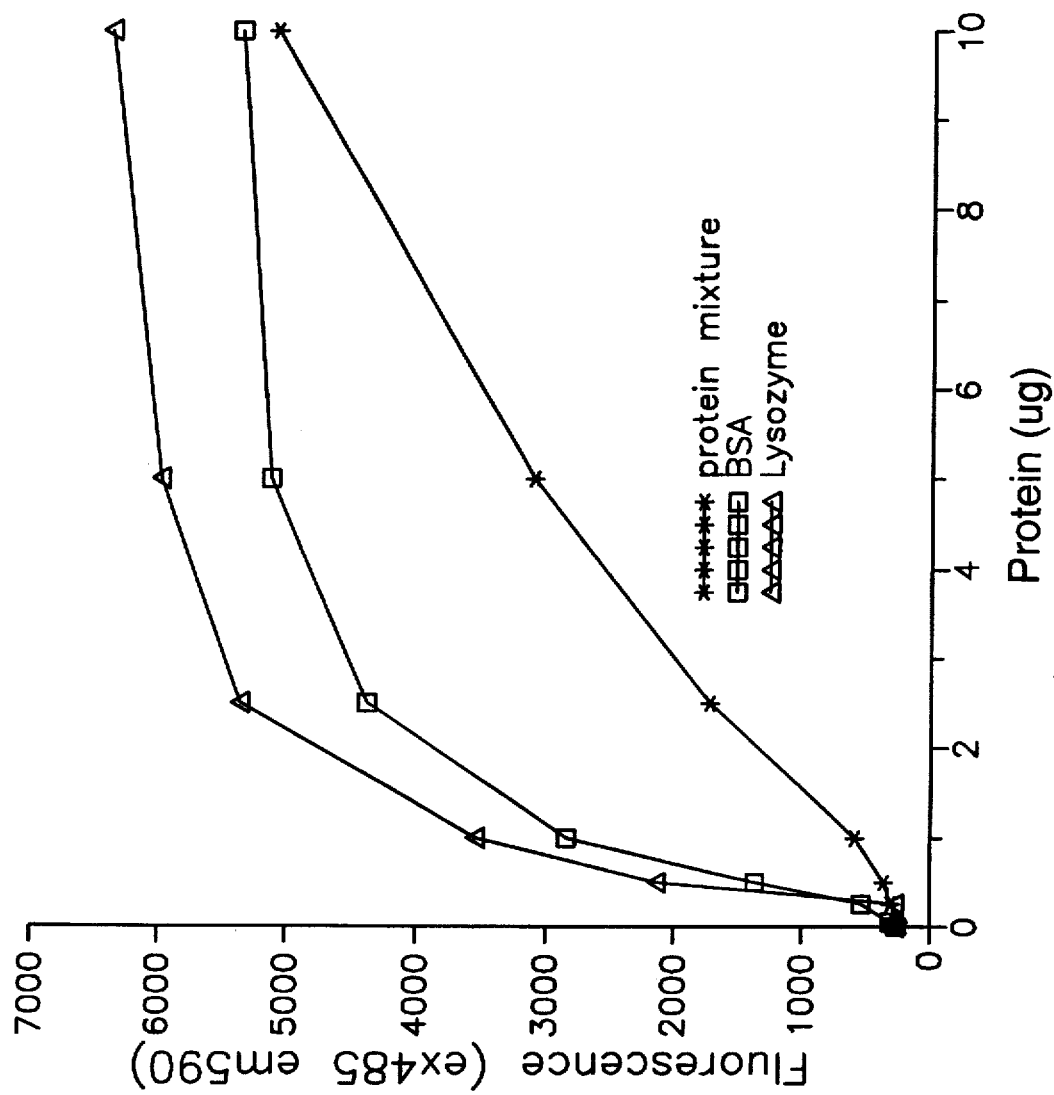
FIG. 4: Correlation between poly(amino acid) concentration and fluorescence emission for Dye 307. The plot was prepared as described in Table 2, note 4, using excitation at 485 nm and recording the fluorescence emission at 590 nm.

Detection of proteins in solution:

A dilution series of proteins is prepared in 10 mM Tris-HCl, pH 7.5, containing 0.05% SDS. An equal volume of a solution containing 2 µM Dye 307 in the same buffer is added to each sample. The samples are incubated for 15 minutes at room temperature, protected from light. The fluorescence intensity of each sample is measured following excitation at 490 nm, using a fluorometer or fluorescence microtiter plate reader. Alternatively, the absorbance of the solution is measured at the wavelength of maximum absorbance for the polypeptide-dye complex. In either case, the fluorescence or absorbance signal obtained from Dye 307 in buffer alone (control) is subtracted from the fluorescence or absorbance recorded for the protein-containing samples in order to determine the intensity of the signal that is due to the presence of protein. Protein concentrations are then determined by comparison of the signal intensity thus obtained with the signals obtained using a dilution series of known concentration prepared using either the same protein or a protein standard, such as bovine serum albumin. FIGS. 3 and 4 show dilution series of several different proteins, including a protein mixture, detected with Dye 601 and Dye 307, respectively.

Example 8

Detection of proteins in gels in the presence of contaminating and nucleic acids:

A whole cell extract from $E.$ $coli$ is prepared using standard methods, by suspending a bacterial cell pellet directly in Loading Buffer and heating it as indicated in Example 1 above. The resulting sample is then pipeted up and down repeatedly, through a fine bore syringe, to shear large DNA molecules. The sample is then diluted serially and loaded onto a denaturing SDS gel in two duplicate dilution series and electrophoresed, as described in Example 1 above. The electrophoresed gel is then cut in half. One half is stained with Dye 304 according to the method of Example 1. The other half is stained with silver according to standard methods. The silver stained haft shows staining of bands that correspond to nucleic acids as well as protein. The half stained with Dye 304 of the present invention exhibits only those bands that result from protein staining.

Example 9

Figure 5:
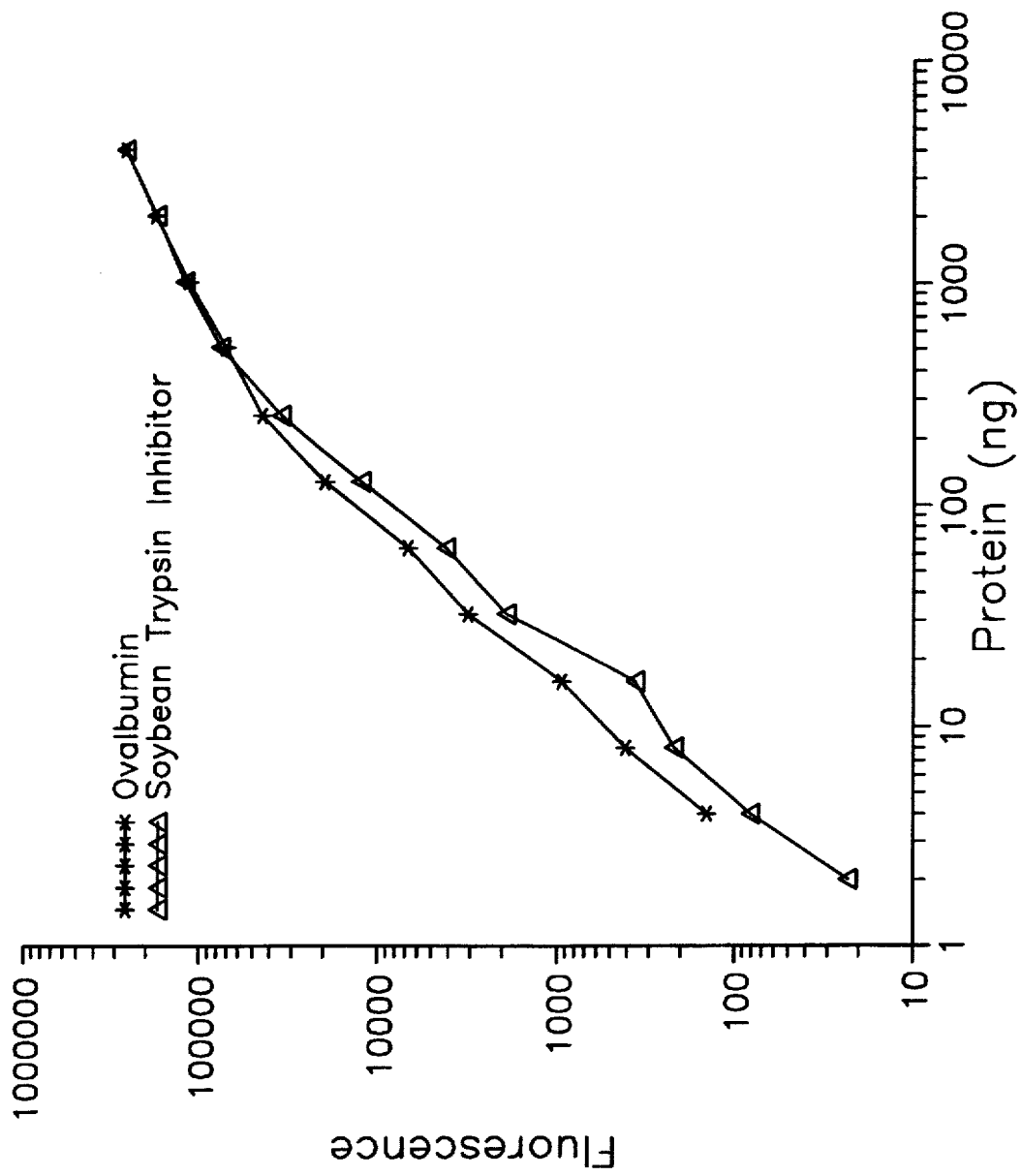
FIG. 5: Correlation between band fluorescence and total poly(amino acids) present in a gel band for Dye 801. The plot was prepared using a standard SDS electrophoretic gel that was scanned using a laser-excited gel scanner, as described in Example 9.
Figure 6:
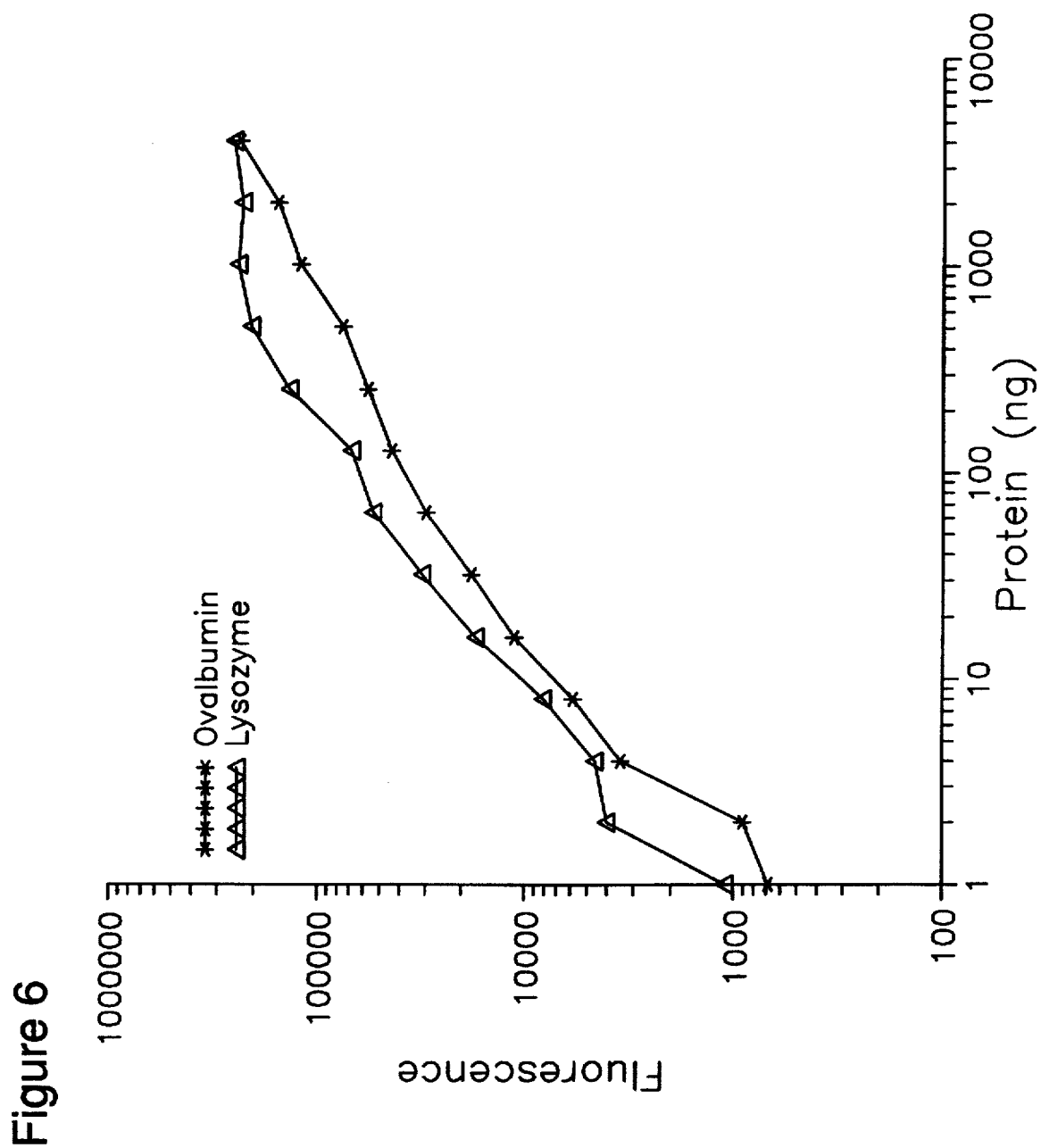
FIG. 6: Correlation between band fluorescence and total poly(amino acids) present in a gel band for Dye 402. The plot was prepared using a standard SDS electrophoretic gel that was scanned using a laser-excited gel scanner, as described in Example 9.

Detection of proteins in gels using a laser-excited gel scanner:

Gels are prepared and stained as described in Examples 1,2, 3 or 4. The resulting stained gels are then scanned using a laser-excited gel scanner, such as the FMBIO-100 (Hitachi Software Engineering America, Ltd., San Bruno, Calif.) or the FLUORIMAGER (Molecular Dynarmes, Inc., Sunnyvale, Calif.). Typical results of this procedure are shown in FIGS. 5 and 6. As indicated in Table 2, the dyes of the present invention, when combined with proteins, display fluorescence emission having a linear dynamic range of at least 3 orders of magnitude in protein concentration, with a sensitivity on the order of a single ng per protein band. Stained gels can be analyzed in this way using visible light lasers that excite at about 488 nm or about 530 nm, as well as with other scanners that have light sources that overlap with the excitation spectra for the specific dye used (see Table 2).

Example 10

Detection of proteins in gels using a CCD camera:

Gels are prepared and stained as described in Examples 1,2, 3 or 4. The resulting stained gels are documented using a CCD camera in combination with ultraviolet transillumination at 300 nm EAGLE EYE still video system, Stratagene Cloning Systems, La Jolla, Calif.).

Example 11

Detection of proteins in isoelectric focusing gels:

A dilution series of isoelectric focusing standards is prepared in water and the samples are loaded onto a standard isoelectric focusing gel (available commercially from Bio-Rad, Hercules, Calif.). The gel is electrophoresed under standard conditions suggested by the manufacturer, then stained with Dye 304 as described in Example 1 above. Proteins are then detected as described in Example 1.

Example 12

Detection of proteins spotted onto a thin layer chromatography plate or filter membrane, by color and fluorescence:

Dilution series of BSA, lysozyme and an equi-mass mixture of myosin, β-galactosidase, phosphorylase B, bovine serum albumin, ovalbumin, carbonic anhydrase, trypsin inhibitor, lysozyme and aprotinin are prepared in 10 mM Tris-HCl, pH 7.5, containing 0.05% SDS. An equal volume of a dye solution containing Dye 803, prepared in the same solution, is added to each and the samples are allowed to incubate for 15 minutes, protected from light. A 1–5 μL aliquot of each mixture is spotted onto a thin layer chromatography plate or a nylon or nitrocellulose filter membrane. Protein-containing spots are either detected colormetrically, under normal room lighting, or are detected by fluorescence following ultraviolet illumination with either a hand-lamp or a trans- or epi-illuminator. The color intensity or fluorescence intensity of a given spot is indicative of the amount of protein present in that spot. The amount of protein in an unknown sample is then determined by comparing either the colorimetric intensity or the fluorescence intensity of the sample with that possessed by a standard of known concentration.

Example 13

Staining protein gels with dye in the running buffer:

The proteins of interest are prepared for loading on standard SDS gels, using standard methods. Dilution series of known molecular weight markers, or proteins of unknown concentration, or protein mixtures of unknown composition are used. The gels are loaded and run under standard conditions, excepting that the running buffer contains 0.05% SDS and 1–3 μM Dye 801. The stained gels are either photographed directly after electrophoresis (as described above in Example 1) or are destained in 7.5% acetic acid for 20–50 minutes to remove background staining prior to photography. The sensitivity obtained using this procedure is about the same as that obtained by staining gels after electrophoresis. In addition, the migration of protein bands can be monitored through the glass plates that support the gel, during electrophoresis. Such monitoring can either be colorimetric, since the stained protein bands are visually colored, or can be via fluorescence, if the excitation source is at visible wavelengths (such as a laser or mercury arc lamp, for example).

Example 14

Prestaining of proteins prior to electrophoresis:

The proteins of interest are diluted to appropriate concentrations in Loading Buffer. The samples are then heated to 90°–95° C. for 4–5 minutes and allowed to cool to room temperature. Dye 304 is added to the protein solutions to a final concentration of 10 mM, and the samples are loaded onto a 12% polyacrylamide gel, or other appropriate percentage gel. The gel is electrophoresed under standard conditions and visualized directly using ultraviolet illumination as described in Example 1. Alternatively, staining can be observed using the methods described in Examples 9 and 10. The sensitivity of this method is somewhat less than the sensitivity possible using the methods in Example 1 (post staining the gel after electrophoresis) or Example 13 (dye in running buffer).

It is to be understood that, while the foregoing invention has been described in detail by way of illustration and example, numerous modifications, substitutions, and alterations are possible without departing from the spirit and scope of the invention as described in the following claims.

What is claimed is:

1. A method of detecting a poly(amino acid), comprising the steps of:

a) combining a sample mixture that is thought to contain a poly(amino acid) with a staining mixture that contains one or more merocyanine dyes to form a combined mixture; wherein each merocyanine dye independently has the formula

Q-B-M where Q is a nitrogen heterocycle of the formula

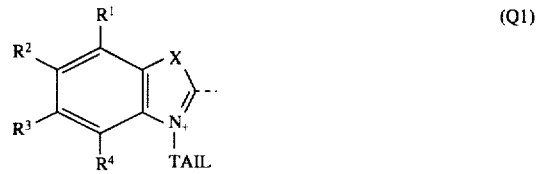

(Q1)

or

(Q2)

or

(Q3)

where $R^1$, $R^2$, $R^3$ and $R^4$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls:

$R^5$ and $R^6$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls: or $R^5$ and $R^6$ taken in combination form a fused 6-membered aromatic ring that is optionally and independently substituted one or more times by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls, or said fused 6-membered aromatic ring is optionally substituted by an additional fused 6-membered aromatic ring that is optionally and independently substituted by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls;

X is —S—, —O—, —NR$^7$—, or —CR$^7$R$^8$—, wherein R$^7$ and R$^8$ are optionally and independently H, Cl, F, phenyl, $C_1$–$C_6$ alkyl.; or R$^7$ and R$^8$ taken in combination complete a 5- or 6-membered saturated fine:

TAIL is attached to Q through a carbon atom and contains 1–22 non-hydrogen atoms, wherein said non-hydrogen atoms are selected from the group consisting of C, O, N and S, such that each heteroatom is separated from any adjacent heteroatoms by at least two carbon atoms: and further such that TAIL is composed of carbon-carbon bonds (C—C), ether bonds (C—O—C), thioether bonds (C—S—C) or amine bonds (C—NR$^9$—C); where any carbon atom in TAIL is optionally further substituted by hydroxy, carboxy, sulfo, amino or ammonium; and where any amine bond, amino or ammonium in TAIL is optionally substituted by an R$^9$ that is a $C_2$-$C_6$ alkyl that is optionally further substituted by hydroxy, carboxy, sulfo, amino, amino substituted by 1-2 $C_1$-$C_6$ alkyls, or ammnonium substituted by 1-3 $C_1$-$C_6$ alkyls, or said N atoms form either one or two saturated 5- or 6-membered rings in combination with additional C or N atoms in TAIL;

B is a covalent bridge having the formula

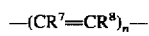

where R$^7$ and R$^8$ are as defined previously;
n=1, 2 or 3;

and M is an electron pair-donating moiety of the formula

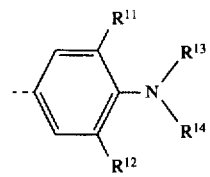
(M1)

or

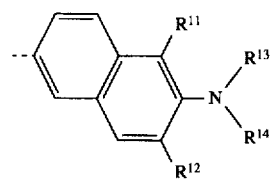
(M2)

where

R$^{11}$ and R$^{12}$ are independently H, F, Cl, or —CH$_3$;

R$^{13}$ and R$^{14}$ are independently $C_1$-$C_{18}$ alkyl that is linear, branched, saturated or unsaturated, and is optionally substituted one or more times by F, hydroxy or $C_1$-$C_6$ alkoxy; or R$^{13}$ and R$^{14}$ taken in combination form a 5- or 6-membered saturated ring containing 0 or 1 oxygen heteroatoms; or R$^{13}$ taken in combination with R$^{11}$ and R$^{14}$ taken in combination with R$^{12}$ independently are —(CH$_2$)$_2$— or —(CH$_2$)$_3$—;

or M is of the formula

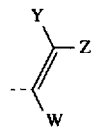
(M3)

where Y is —OH, —SH, —O$^-$ or —S$^-$;
Z is —OR$^{15}$, —SR$^{15}$, —N(R$^{15}$)$_2$;
W is CN, —(C=O)—R$^{16}$, or —(C=S)—R$^{16}$;
R$^{15}$ is H or $C_1$-$C_6$ alkyl;

R$^{16}$ is —OR$^{15}$, —SR$^{15}$, —N(R$^{15}$)$_2$;
or M is of the formula

(M4)

where Y is as defined previously;
Z' is —O—, —S—, or —NR$^{17}$—;
W' is —O—, —S—, —NR$^{17}$—, —(C=O)—, —(C=S)—, or —(C=NR$^{17}$)—;
R$^{17}$ is H, $C_1$-$C_6$ alkyl, $C_1$-$C_6$ carboxyalkyl, phenyl or phenyl substituted by sulfo;
R$^{18}$ is —O—, —S—, —NR$^{17}$—, —(C=O)—, —(C=S)—, or —(C=NR$^{17}$)—;
or W' and R$^{18}$ taken in combination are —CR$^{17}$=N—;
or Z' and R$^{18}$ taken in combination are —CR$^{17}$=N—;
or M is of the formula

(M5)

where Y and Z' are as defined previously;
W" is —(C=O)—, —(C=S)—, or —(C=NR$^{17}$)—;
L is —(C=O)—, or —(C=S)—;
R$^{19}$ is —O—, —S—, —NR$^{17}$—;
or W" and R$^{19}$ taken in combination are —CR$^{17}$=N—;
such that the resulting heterocycle does not include any O—O, S—S, O—S, or N—N—N bonds;

b) heating tile sample mixture prior to combining with the staining mixture, or heating the combined mixture:

c) incubating the combined mixture for a time sufficient for the dye in the staining mixture to associate with the poly(amino acid) in the sample mixture to form a dye-poly(amino acid) complex that gives a detectable optical response upon illumination;

d) illuminating said dye-poly(amino acid) complex; and e) observing said detectable optical response.

2. A method, as claimed in claim 1, wherein for at least one merocyanine dye, M has the formula M1.

3. A method, as claimed in claim 1, wherein for at least one merocyanine dye, M has the formula M2.

4. A method, as claimed in claim 1, wherein for at least one merocyanine dye, M has the formula M3, M4 or M5.

5. A method, as claimed in claim 1, wherein for at least one merocyanine dye,

TAIL is —CH$_3$, or CH$_2$CH$_3$; or TAIL is a $C_3$-$C_{22}$ alkyl chain that is linear or branched, saturated or unsaturated, that is optionally substituted one or more times by hydroxy, carboxy, sulfo, amino, amino substituted by 1-2 $C_1$-$C_6$ alkyls, or ammonium substituted by 1-3 $C_1$-$C_6$ alkyls.

6. A method, as claimed in claim 1, wherein for at least one merocyanine dye,

M has the formula M1 or M2;
X is O or S;
B is —(CH=CH)$_n$—;
n=1 or 2;
R$^1$, R$^2$, R$^3$, R$^4$, R$^{11}$ and R$^{12}$ are each H;
R$^5$ and R$^6$ are each H, or R$^5$ and R$^6$, taken in combination, form a fused 6-membered aromatic ring;
R$^{13}$ and R$^{14}$ are independently $C_4$-$C_8$ alkyl; and TAIL is sulfopropyl, sulfobutyl, aminopropyl or aminobutyl, the amines of which are substituted 1–3 times by any combination of H, methyl or ethyl;

wherein said merocyanine dye is present in the combined mixture at a concentration of 0.10 μM–10 μM for a fluorescent optical response or 10 μM–100 μM for colorimetric optical response; and said poly(amino acid) has a molecular weight of 500–200,000 daltons.

7. A method, as claimed in claim 1, further comprising adding a detergent to the sample mixture, staining mixture or combined mixture.

8. A method, as claimed in claim 7, wherein said detergent is an alkyl sulfate or alkyl sulfonate salt having 6–18 carbons; that is present in a concentration of less than 0.1% by weight.

9. A method, as claimed in claim 1, wherein said detectable optical response is a fluorescence response.

10. A method, as claimed in claim 1, further comprising quantitating said poly(amino acid) by measuring said detectable optical response and comparing said measurement with a standard.

11. A method, as claimed in claim 1, further comprising electrophoretically separating the sample mixture before, after, or while it is combined with the staining mixture.

12. A method, as claimed in claim 1, wherein the step of heating comprises heating the sample mixture to at least 90° C.

13. A combination consisting essentially of:

a) one or more styryl dyes having the formula

Q-B-M where Q is a nitrogen heterocycle of the formula

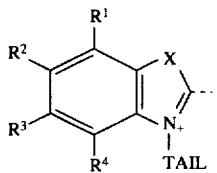 (Q1)

or

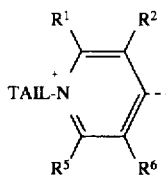 (Q2)

or

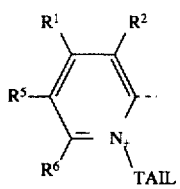 (Q3)

where $R^1$, $R^2$, $R^3$ and $R^4$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls;

$R^5$ and $R^6$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls; or $R^5$ and $R^6$ taken in combination form a fused 6-membered aromatic ring that is optionally and independently substituted one or more times by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls, or said fused 6-membered aromatic ring is optionally substituted by an additional fused 6-membered aromatic ring that is optionally and independently substituted by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls;

X is —S—, —O—, —$NR^7$—, or —$CR^7R^8$—, wherein $R^7$ and $R^8$ are optionally and independently H, Cl, F, phenyl, $C_1$–$C_6$ alkyl; or $R^7$ and $R^8$ taken in combination complete a 5- or 6-membered saturated ring;

TAIL is attached to Q through a carbon atom and contains 1–22 non-hydrogen atoms, wherein said non-hydrogen atoms are selected from the group consisting of C, O, N and S, such that each heteroatom is separated from any adjacent heteroatoms by at least two carbon atoms; and further such that TAIL is composed of carbon-carbon bonds (C—C), ether bonds (C—O—C), thioether bonds (C—S—C) or amine bonds (C—$NR^9$—C); where any carbon atom in TAIL is optionally further substituted by hydroxy, carboxy, sulfo, amino or ammonium; and where any amine bond, amino or ammonium in TAIL is optionally substituted by an $R^9$ that is a $C_2$–$C_6$ alkyl that is optionally further substituted by hydroxy, carboxy, sulfo, amino, amino substituted by 1–2 $C_1$–$C_6$ alkyls, or ammonium substituted by 1–3 $C_1$–$C_6$ alkyls, or said N atoms form either one or two saturated 5- or 6-membered rings in combination with additional C or N atoms in TAIL;

B is a covalent bridge having the formula

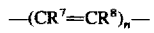

—(CR$^7$=CR$^8$)$_n$— where $R^7$ and $R^8$ are as defined previously; n=1, 2 or 3;

and M is an electron pair-donating moiety of the formula

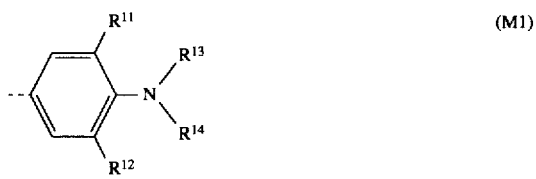 (M1)

or

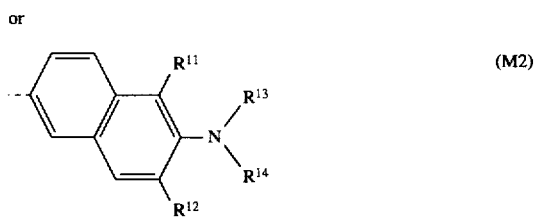 (M2)

where $R^{11}$ and $R^{12}$ are independently H, F, Cl, or —$CH_3$;

$R^{13}$ and $R^{14}$ are independently $C_1$–$C_{18}$ alkyl that is linear, branched, saturated or unsaturated, and is optionally substituted one or more times by F, hydroxy or $C_1$–$C_6$ alkoxy; or $R^{13}$ and $R^{14}$ taken in combination form a 5- or 6-membered saturated ring containing 0 or 1 oxygen heteroatoms;

or $R^{13}$ taken in combination with $R^{11}$ and $R^{14}$ taken in combination with $R^{12}$ independently are —(CH$_2$)$_2$— or —(CH$_2$)$_3$—;

b) a detergent; and c) a poly(amino acid), in a cell-free aqueous solution where said detergent is present at a concentration less than the critical micelle concentration for that detergent.

14. A combination, as claimed in claim 13, where for at least one of said styryl dyes, Q has the formula Q2.

15. A combination, as claimed in claim 13, where said detergent is an alkyl sulfate or alkyl sulfonate salt.

16. A kit for staining the poly(amino acids) in a sample, comprising:

a) one or more merocyanine dyes, wherein each merocyanine dye independently has the formula

Q-B-M where Q is a nitrogen heterocycle of the formula

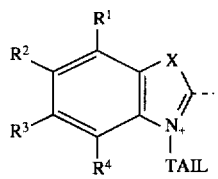
(Q1)

or

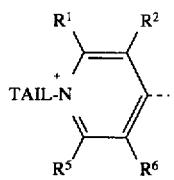
(Q2)

or

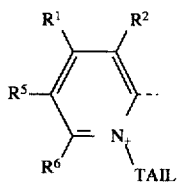
(Q3)

where $R^1$, $R^2$, $R^3$ and $R^4$ are optionally and independently H, Cl, F, $C_1$–$C_6$ alkyl, $C_1$–$C_6$ perfluoroalkyl, $C_1$–$C_6$ alkoxy, amino or amino substituted by 1–2 $C_1$–$C_6$ alkyls;

$R^5$ and $R^6$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls; or $R^5$ and $R^6$ taken in combination form a fused 6-membered aromatic ring that is optionally and independently substituted one or more times by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls, or said fused 6-membered aromatic ring is optionally substituted by an additional fused 6-membered aromatic ring that is optionally and independently substituted by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls;

X is —S—, —O—, —$NR^7$—, or —$CR^7R^8$—, wherein $R^7$ and $R^8$ are optionally and independently H, Cl, F, phenyl, $C_1$–$C_6$ alkyl,; or $R^7$ and $R^8$ taken in combination complete a 5- or 6-membered saturated ring;

TAIL is attached to Q through a carbon atom and contains 1–22 non-hydrogen atoms, wherein said non-hydrogen atoms are selected from the group consisting of C, O, N and S, such that each heteroatom is separated from any adjacent heteroatoms by at least two carbon atoms; and further such that TAIL is composed of carbon-carbon bonds (C—C), ether bonds (C—O—C), thioether bonds (C—S—C) or amine bonds (C—$NR^9$—C): where any carbon atom in TAIL is optionally further substituted by hydroxy, carboxy, sulfo, amino or ammonium; and where any amine bond, amino or ammonium in TAIL is optionally substituted by an $R^9$ that is a $C_2$–$C_6$ alkyl that is optionally further substituted by hydroxy, carboxy, sulfo, amino, amino substituted by 1–2 $C_1$–$C_6$ alkyls, or ammonium substituted by 1–3 $C_1$–$C_6$ alkyls, or said N atoms form either one or two saturated 5- or 6-membered rings in combination with additional C or N atoms in TAIL;

B is a covalent bridge having the formula

—$(CR^7=CR^8)_n$— where $R^7$ and $R^8$ are as defined previously;

n=1, 2 or 3;

and M is an electron pair-donating moiety of the formula

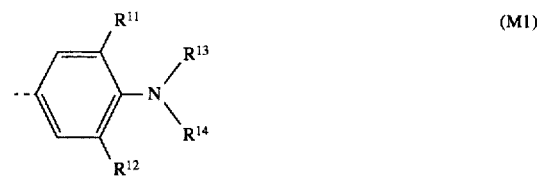
(M1)

or

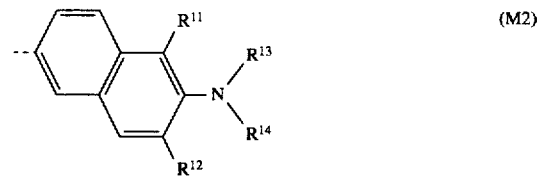
(M2)

where $R^{11}$ and $R^{12}$ are independently H, F, Cl, or —$CH_3$;

$R^{13}$ and $R^{14}$ are independently $C_1$–$C_{18}$ alkyl that is linear, branched, saturated or unsaturated, and is optionally substituted one or more times by F, hydroxy or $C_1$–$C_6$ alkoxy; or $R^{13}$ and $R^{14}$ taken in combination form a 5- or 6-membered saturated ring containing 0 or 1 oxygen heteroatoms; or $R^{13}$ taken in combination with $R^{11}$ and $R^{14}$ taken in combination with $R^{12}$ independently are —$(CH_2)_2$— or —$(CH_2)_3$—;

or M is of the formula

(M3)

where Y is —OH, —SH, —O⁻ or —S⁻;

Z is —$OR^{15}$, —$SR^{15}$, —$N(R^{15})_2$;

W is CN, —(C=O)—$R^{16}$, or —(C=S)—$R^{16}$;

$R^{15}$ is H or $C_1$–$C_6$ alkyl:

$R^{16}$ is —$OR^{15}$, —$SR^{15}$, —$N(R^{15})_2$;

or M is of the formula

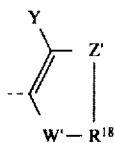 (M4)

where Y is as defined previously:
Z' is —O—, —S—, or —$NR^{17}$—;
W' is —O—, —S—, —$NR^{17}$, —(C=O)—, —(C=S)—, or —(C=$NR^{17}$)—;
$R^{17}$ is H, $C_1$–$C_6$ alkyl, $C_1$–$C_6$ carboxyalkyl, phenyl or phenyl substituted by sulfo;
$R^{18}$ is —O—, —S—, —$NR^{17}$—, —(C=O)—, —(C=S)—, or —(C=$NR^{17}$)—;
or W' and $R^{18}$ taken in combination are —$CR^{17}$=N—;
or Z' and $R^{18}$ taken in combination are —$CR^{17}$=N—;
or M is of the formula

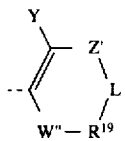 (M5)

where Y and Z' are as defined previously:
W" is —(C=O)—, —(C=S)—, or —(C=$NR^{17}$)—;
L is —(C=O)—, or —(C=S)—;
$R^{19}$ is —O—, —S—, or —$NR^{17}$—;
or W" and $R^{19}$ taken in combination are —$CR^{17}$=N—;
such that the resulting heterocycle does not include any O—O, S—S, O—S, or N—N—N bonds; and b) instructions for combining said merocyanine dye or dyes with a sample containing or thought to contain poly(amino acids),; said instructions comprising
  i) combining a sample that is thought to contain a poly(amino acid) with a staining mixture that contains said merocyanine dye or dyes to form a combined mixture;
  ii) incubating the combined mixture for a time sufficient for the dye in the staining mixture to associate with the poly(amino acid) in the sample mixture to form a dye-poly(amino acid) complex that gives a detectable optical response upon illumination.

17. A kit, as claimed in claim 14, where said instructions further spcify subjecting said sample to electrophoresis before, during or after being combined with said dye or dyes.

18. A kit, as claimed in claim 16, wherein each of said merocyanme dyes has the formula

Q-B-M where Q is a nitrogen heterocycle of the formula

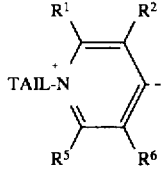 (Q2)

where
$R^1$ and $R^2$ are H;
$R^5$ and $R^6$ are optionally and independently H, Cl, F, $C_1$–$C_6$ alkyl, $C_1$–$C_6$ perfluoroalkyl, $C_1$–$C_6$ alkoxy, amino or amino substituted by 1–2 $C_1$–$C_6$ alkyls; or $R^5$ and $R^6$ taken in combination form a fused 6-membered aromatic ring that is optionally substituted and independently substituted one or more times by Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls;

TAIL is —$CH_3$, or $CH_2CH_3$; or TAIL is a $C_3$–$C_{22}$ alkyl chain that is linear or branched, saturated or unsaturated, that is optionally substituted one or more times by hydroxy, carboxy, sulfo, amino, amino substituted by 1–2 $C_1$–$C_6$ alkyls, or ammonium substituted by 1–3 $C_1$–$C_6$ alkyls;

B is a covalent bridge having the formula

—(CH=CH)$_n$— wherein n=1 or 2;

and M is an electron pair-donating moiety of the formula

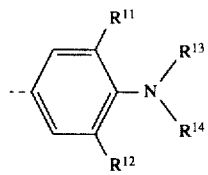 (M1)

or

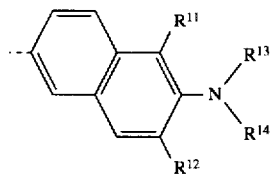 (M2)

where
$R^{11}$ and $R^{12}$ are H;
$R^{13}$ and $R^{14}$ are independently $C_1$–$C_{18}$ alkyl that is linear, branched, saturated or unsaturated, and is optionally substituted one or more times by F.

19. A method of detecting a poly(amino acid), comprising the steps of:
  a) combining a sample mixture that is thought to contain a poly(amino acid) with a staining mixture that contains one or more styryl dyes having the formula

Q-B-M where Q is a nitrogen heterocycle of the formula

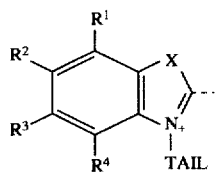 (Q1)

or

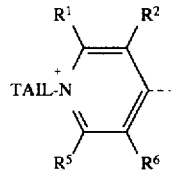 (Q2)

or

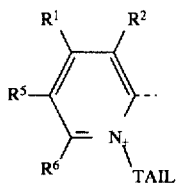

(Q3)

where
- $R^1$, $R^2$, $R^3$ and $R^4$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls;
- $R^5$ and $R^6$ are optionally and independently H, Cl, F, $C_1$–$C_6$ alkyl, $C_1$–$C_6$ perfluoroalkyl, $C_1$–$C_6$ alkoxy, amino, or amino substituted by 1–2 $C_1$–$C_6$ alkyls; or $R^5$ and $R^6$ taken in combination form a fused 6-membered aromatic ring that is optionally and independently substituted one or more times by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls, or said fused 6-membered aromatic ring is optionally substituted by an additional fused 6-membered aromatic ring that is optionally and independently substituted by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls;
- X is —S—, —O—, —$NR^7$—, or —$CR^7R^8$—, wherein $R^7$ and $R^8$ are optionally and independently H, Cl, F, phenyl, $C_1$–$C_6$ alkyl; or $R^7$ and $R^8$ taken in combination complete a 5- or 6-membered saturated ring;
- TAIL is attached to Q through a carbon atom and contains 1–22 non-hydrogen atoms, wherein said non-hydrogen atoms are selected from the group consisting of C, O, N and S, such that each heteroatom is separated from any adjacent heteroatoms by at least two carbon atoms; and further such that TAIL is composed of carbon-carbon bonds (C—C), ether bonds (C—O—C), thioether bonds (C—S—C) or amine bonds (C—$NR^9$—C); where any carbon atom in TAIL is optionally further substituted by hydroxy, carboxy, sulfo, amino or ammonium; and where any amine bond, amino or ammonium in TAIL is optionally substituted by an $R^9$ that is a $C_2$–$C_6$ alkyl that is optionally further substituted by hydroxy, carboxy, sulfo, amino, amino substituted by 1–2 $C_1$–$C_6$ alkyls, or ammonium substituted by 1–3 $C_1$–$C_6$ alkyls, or said N atoms form either one or two saturated 5- or 6-membered rings in combination with additional C or N atoms in TAIL;

B is a covalent bridge having the formula

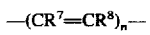

where $R^7$ and $R^8$ are as defined previously;
n=1, 2 or 3;
and M is an electron pair-donating moiety of the formula

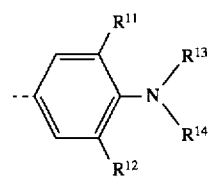

(M1)

or

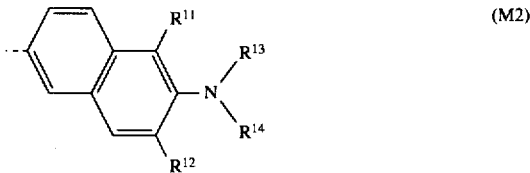

(M2)

where
- $R^{11}$ and $R^{12}$ are independently H, F, Cl, or —$CH_3$;
- $R^{13}$ and $R^{14}$ are independently $C_1$–$C_{18}$ alkyl that is linear, branched, saturated or unsaturated, and is optionally substituted one or more times by F, hydroxy or $C_1$–$C_6$ alkoxy; or $R^{13}$ and $R^{14}$ taken in combination form a 5- or 6-membered saturated ring containing 0 or 1 oxygen heteroatoms; or $R^{13}$ taken in combination with $R^{11}$ and $R^{14}$ taken in combination with $R^{12}$ independently are —$(CH_2)_2$— or —$(CH_2)_3$—;

to form a combined mixture;

b) incubating the combined mixture for a time sufficient for the dye in the staining mixture to associate with the poly(amino acid) in the sample mixture to form a dye-poly(amino acid) complex that gives a detectable optical response upon illumination;

c) illuminating said dye-poly(amino acid) complex; and d) observing said detectable optical response.

20. A method, as claimed in claim 10, wherein for at least one styryl dye, said dye has the formula

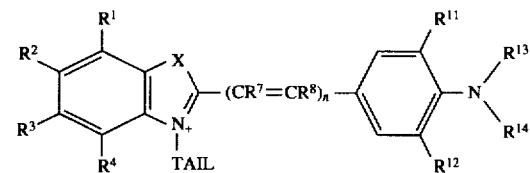

or formula

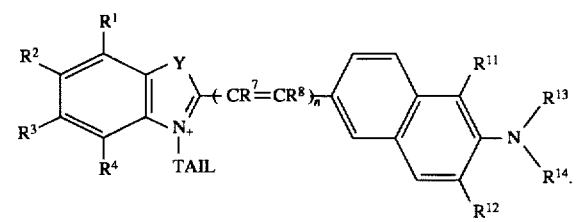

21. A method, as claimed in claim 19, wherein for at least one styryl dye, said dye has the formula

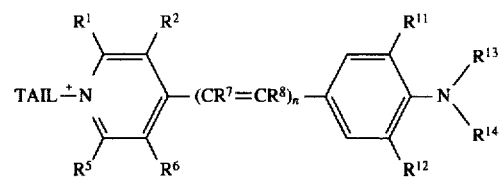

or formula

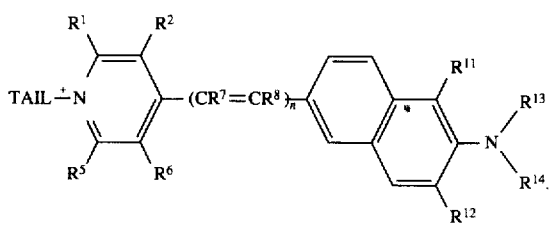

22. A method, as claimed in claim 19, wherein for at least one styryl dye, said dye has the formula

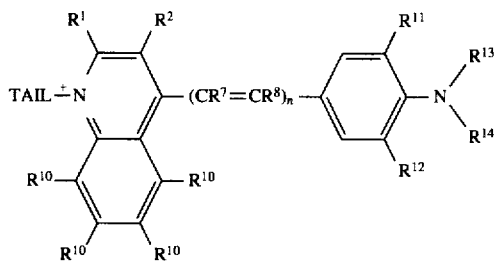

or formula

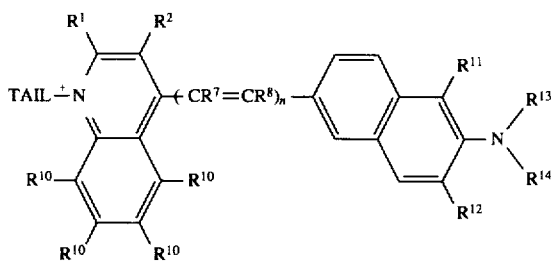

where each $R^{10}$ is independently H, Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls, or any two adjacent $R^{10}$ substituents, when taken in combination, form a fused 6-membered aromatic ring that is optionally and independently substituted by Cl, F, $C_1$–$C_6$ alkyl, $C_1$–$C_6$ perfluoroalkyl, $C_1$–$C_6$ alkoxy, amino, amino substituted by 1–2 $C_1$–$C_6$ alkyls.

23. A method, as claimed in claim 19, wherein for at least one styryl dye,

X is O or S;

B is —(CH=CH)$_n$—;

n=1 or 2;

$R^{11}$ and $R^{12}$ are each H;

$R^{13}$ and $R^{14}$ are independently $C_4$–$C_8$ alkyl; and

TAIL is sulfopropyl, sulfobutyl, aminopropyl or aminobutyl, the amines of which are substituted 1–3 times by any combination of H, methyl or ethyl.

24. A method, as claimed in claim 23, further comprising electrophoretically separating the sample mixture before, after, ir while it is combined with the staining mixture.

25. A method, as claimed in claim 19, further comprising removing, destroying, or dispersing below the critical micelle concentration any biological membranes that are present in the sample mixture.

26. A method, as claimed in claim 19, further comprising adding a detergent to the sample mixture, staining mixture or combined mixture, wherein said detergent is an anionic detergent.

27. A method, as claimed in claim 19, further comprising transferring the sample mixture to a solid or semi-solid matrix before or after combining with the staining mixture.

28. A method, as claimed in claim 19, further comprising adding an additional reagent to the sample mixture, the staining mixture, or the combined mixture.

29. A method, as claimed in claim 19, wherein for at least one styryl dye,

TAIL is —CH$_3$, or CH$_2$CH$_3$; or TAIL is a $C_3$–$C_{22}$ alkyl chain that is linear or branched, saturated or unsaturated, that is optionally substituted one or more times by hydroxy, carboxy, sulfo, amino, amino substituted by 1–2 $C_1$–$C_6$ alkyls, or ammonium substituted by 1–3 $C_1$–$C_6$ alkyls.

30. A method, as claimed in claim 19, wherein said detectable optical response is a fluorescence response.

31. A method, as claimed in claim 19, further comprising electrophoretically separating the sample mixture before, after, or while it is combined with the staining mixture.

32. A method, as claimed in claim 31, wherein said detectable optical response is a colorimetric response.

33. A method, as claimed in claim 31, wherein according to the formula for one styryl dye, Q has the formula Q1.

34. A method, as claimed in claim 31, wherein according to the formula for one styryl dye, Q has the formula Q2.

35. A method, as claimed in claim 31, wherein according to the formula for one styryl dye, Q has the formula Q3.

36. A method, as claimed in claim 31, further comprising the steps of adding a detergent to the sample mixture, staining mixture or combined mixture; and heating the sample mixture prior to combining with the staining mixture, or heating the combined mixture.

37. A method, as claimed in claim 31, wherein said styryl dye has a detection sensitivity of 10 or less ng of poly(amino acid) per band upon illumination at a wavelength at or near the wavelength of maximum absorption of the dye-poly(amino-acid) complex.

38. A method, as claimed in claim 19, further comprising quantitating said poly(amino acid) by measuring said detectable optical response and comparing said measurement with a standard.

* * * * *

UNITED STATES PATENT AND TRADEMARK OFFICE
CERTIFICATE OF CORRECTION

PATENT NO. : 5,616,502

DATED : April 1, 1997

INVENTOR(S) : Haugland, et al.

It is certified that error appears in the above-indentified patent and that said Letters Patent is hereby corrected as shown below:

At column 4, lines 27 to 33, the formula reading

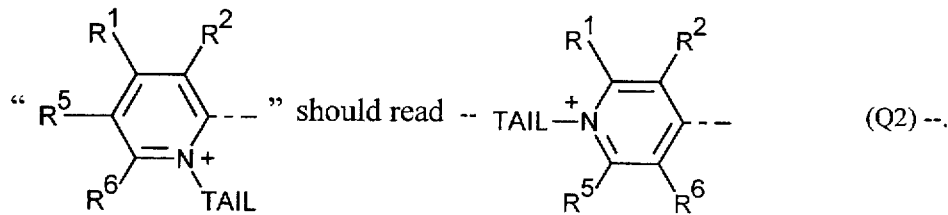

At column 4, lines 37 to 43, the formula reading

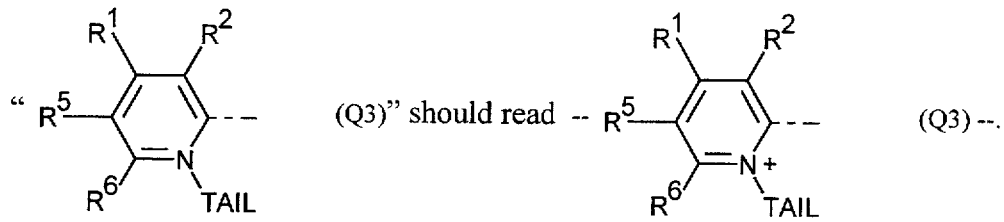

UNITED STATES PATENT AND TRADEMARK OFFICE
CERTIFICATE OF CORRECTION

PATENT NO. : 5,616,502
DATED : April 1, 1997
INVENTOR(S) : Haugland, et al.

It is certified that error appears in the above-indentified patent and that said Letters Patent is hereby corrected as shown below:

At column 6, line 24 "ting" should be --ring--.

At column 19, line 8 "/br" should be --for--.

At column 20, line 17 "pretizrably" should be --preferably--.

At column 21, line 51 "e,exhibit" should be --exhibit--.

At column 23, line 27 "elcctrophoresis" should be --electrophoresis--.

At column 24, line 5 "elcctrophoretic" should be --electrophoretic--.

At column 25, line 44 "fight" should be --light--.

At column 31, line 24 "anaino" should be --amino--.

At column 37, line 65 "-N($R^{15}$)$^2$" should be ---N($R^{15}$)$_2$--

At column 38, line 34 "tile" should be --the--.

UNITED STATES PATENT AND TRADEMARK OFFICE
CERTIFICATE OF CORRECTION

PATENT NO. : 5,616,502
DATED : April 1, 1997
INVENTOR(S) : Haugland, et al.

It is certified that error appears in the above-indentified patent and that said Letters Patent is hereby corrected as shown below:

At column 42, line 66 "iS" should be --is--.

At column 43, line 35 "acids).;" should be --acids);--

At column 44, line 36 "*are H;*" should be --are H;--.

At column 46, line 35 "claim 10" should be --claim 19--.

At column 48, line 3 "ir" should be --or--.

Signed and Sealed this

Eighth Day of July, 1997

BRUCE LEHMAN

Attest:

*Attesting Officer*      Commissioner of Patents and Trademarks